US011147899B2

(12) United States Patent
Levenberg et al.

(10) Patent No.: US 11,147,899 B2
(45) Date of Patent: Oct. 19, 2021

(54) FLAP FOR DE-NOVO TISSUE REGENERATION

(71) Applicants: TECHNION RESEARCH & DEVELOPMENT FOUNDATION LIMITED, Haifa (IL); HEALTH CORPORATION-RAMBAM, Haifa (IL)

(72) Inventors: Shulamit Levenberg, Moreshet (IL); Dana Egozi, Haifa (IL); Jacob Koffler, Tel-Aviv (IL); Yulia Shandalov-Levi, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 290 days.

(21) Appl. No.: 14/916,226

(22) PCT Filed: Sep. 2, 2014

(86) PCT No.: PCT/IL2014/050784
§ 371 (c)(1),
(2) Date: Mar. 3, 2016

(87) PCT Pub. No.: WO2015/033337
PCT Pub. Date: Mar. 12, 2015

(65) Prior Publication Data
US 2016/0193382 A1 Jul. 7, 2016

(30) Foreign Application Priority Data
Sep. 3, 2013 (IL) .......................................... 228284

(51) Int. Cl.
| | | |
|---|---|---|
| A61L 27/18 | (2006.01) | |
| C12N 5/077 | (2010.01) | |
| A61L 27/36 | (2006.01) | |
| A61L 27/56 | (2006.01) | |
| A61L 27/38 | (2006.01) | |
| C12N 5/071 | (2010.01) | |

(52) U.S. Cl.
CPC .......... *A61L 27/18* (2013.01); *A61L 27/3625* (2013.01); *A61L 27/3695* (2013.01); *A61L 27/3808* (2013.01); *A61L 27/3886* (2013.01); *A61L 27/3895* (2013.01); *A61L 27/56* (2013.01); *C12N 5/069* (2013.01); *C12N 5/0658* (2013.01); *A61L 2300/64* (2013.01); *A61L 2430/34* (2013.01); *C12N 2502/13* (2013.01); *C12N 2502/1335* (2013.01); *C12N 2533/40* (2013.01)

(58) Field of Classification Search
None
See application file for complete search history.

(56) References Cited

U.S. PATENT DOCUMENTS

| | | | | |
|---|---|---|---|---|
| 8,043,614 B2* | 10/2011 | Ahlfors | ............... | A61L 27/3633 424/93.1 |
| 2006/0136068 A1 | 6/2006 | de Bruijn et al. | | |
| 2006/0198827 A1* | 9/2006 | Levenberg | ........... | C12N 5/0657 424/93.7 |
| 2007/0299508 A1* | 12/2007 | Morrison | ................ | A61F 2/062 623/1.41 |
| 2013/0030548 A1* | 1/2013 | Ling | ....................... | A61F 2/105 623/23.72 |

FOREIGN PATENT DOCUMENTS

| | | |
|---|---|---|
| WO | 9308850 A1 | 5/1993 |
| WO | 0215914 A1 | 2/2002 |
| WO | 2012111000 A1 | 8/2012 |

OTHER PUBLICATIONS

Encyclopedia . com, 2001, https://www.encyclopedia.com/medicine/anatomy-and-physiology/anatomy-and-physiology/blood-vessels , pp. 1-8. (Year: 2001).*
Huang et al., "Multilineage Differentiation Potential of Fibroblast-like Stromal Cells Derived from Human Skin", Tissue Engineering: Part A, 2010, vol. 16, No. 5, pp. 1491-1501 (Year: 2010).*
Lesman et al., "Engineering vessel-like networks within multicellular fibrin-based constructs", Biomaterials, 2011, vol. 32, pp. 7856-7869. (Year: 2011).*
Shevchenko et al., "A review of tissue-engineered skin bioconstructs available for skin reconstruction", Journal of the Royal Society Interface, 2010, vol. 7, pp. 229-258 (Year: 2010).*
Venkatramani et al., "Fingertip replantation: Technical considerations and outcome analysis of 24 consecutive fingertip replantations", Indian Journal of Plastic Surgery, 2011, 44(2):237-245 (Year: 2011).*
Sawh Martinez, Rajendra Fernando, "Understanding the Development of Tissue Engineered Blood Vessels", Yale Medicine Thesis Digital Library, 1592, 2011, pp. cover page, 1-82. (Year: 2011).*
Gerard et al., "Facilitating tissue infiltration and angiogenesis in a tubular collagen scaffold", Journal of Biomedical Materials Research Part A, 2009, 93(2), pp. 615-624. (Year: 2009).*
Tanaka et al., "Tissue Engineering Skin Flaps: Which Vascular Carrier, Arteriovenous Shunt Loop or Arteriovenous Bundle, Has More Potential for Angiogenesis and Tissue Generation?", Plastic and Reconstructive Surgery, 2003, 112(6), pp. 1636-164. (Year: 2003).*
Pevec et al., "New blood vessels can be ischemic skeletal muscle induced to invade", Journal of Vascular Surgery, 1996, vol. 24, pp. 534-544. (Year: 1996).*

(Continued)

*Primary Examiner* — Laura Schuberg
(74) *Attorney, Agent, or Firm* — Roach Brown McCarthy & Gruber; Kevin D. McCarthy

(57) ABSTRACT

The present invention provides an implant which includes: (a) an autologous engineered tissue; and (b) a vasculature, wherein the engineered tissue is a porous scaffold embedded with endothelial cell, a fibroblast, a myoblast, a mesenchymal cell, an adipocyte, or any combination thereof, wherein the vasculature feeds the cells. Further, the invention provides a method for treating a subject afflicted with a large soft tissue defect by implanting the implant of the invention.

14 Claims, 9 Drawing Sheets
(5 of 9 Drawing Sheet(s) Filed in Color)

(56) References Cited

OTHER PUBLICATIONS

Internatianal Search Report from a counterpart foreign application—PCT/IL2014/050784—dated Jan. 16, 2015, 4 pages.
Written Opinion of the International Searching Authority from a counterpart foreign application—PCT/IL2014/050784—dated Jan. 16, 2015, 8 pages.
Harvey N. Mayrovitz: "Skin Capillary Metrics and Hemodynamics in the Hairless Mouse", Microvascular Research, vol. 43, pp. 46-59, (1992).
Shigehiko Suzuki et al: "Clinical evaluation of a new bilayer "artificial skin" composed of collagen sponge and silicone layer", British Journal of Plastic Surgery, (1990), vol. 43, pp. 47-54.
https://www.ncbi.nlm.nih.gov/books/NBK26848/, copyrighted in 1983—6 pages.

\* cited by examiner

FLAP FOR DE-NOVO TISSUE REGENERATION

FIELD OF INVENTION

This invention is directed to; inter alia, implants composed of cellular scaffolds and a vascular pedicle.

BACKGROUND OF THE INVENTION

In the United States alone, approximately 25% of patients in need of organ transplants die while waiting for a suitable donor. The current demands for transplant organs and tissues are far outpacing the supply, and all manner of projections indicate that this gap will continue to widen. Cell transplantation was proposed as an alternative treatment to whole organ transplantation for failing or malfunctioning organs. For the creation of an autologous implant, donor tissue is harvested and dissociated into individual cells, and the cells are attached and cultured onto a proper substrate that is ultimately implanted at the desired site of the functioning tissue. Because many isolated cell populations can be expanded in-vitro using cell culture techniques, only a very small number of donor cells may be necessary to prepare such implants. However, it is believed that isolated cells cannot form new tissues, independently. Most primary cells are believed to be anchorage-dependent and require specific environments that very often include the presence of a supporting material to act as a template for growth. The success of any cell transplantation therapy therefore relies on the development of suitable substrates for both in-vitro and in-vivo tissue culture.

Tissue engineering applications or even in 3D cell cultures, the biological cross talk between cells and the scaffold is controlled by the material properties and scaffold characteristics. In order to induce cell adhesion, proliferation, and activation, materials used for the fabrication of scaffolds must possess requirements such as intrinsic biocompatibility and proper chemistry to induce molecular bio-recognition from cells. Materials, scaffold mechanical properties and degradation kinetics should be adapted to the specific tissue engineering application to guarantee the required mechanical functions and to accomplish the rate of the new-tissue formation. For scaffolds, pore distribution, exposed surface area, and porosity play a major role, whose amount and distribution influence the penetration and the rate of penetration of cells within the scaffold volume, the architecture of the produced extracellular matrix, and for tissue engineering applications, the final effectiveness of the regenerative process. Depending on the fabrication process, scaffolds with different architecture can be obtained, with random or tailored pore distribution. In the recent years, rapid prototyping computer-controlled techniques have been applied to the fabrication of scaffolds with ordered geometry (Carletti E, Motta A, and Migliaresi C. Scaffolds for tissue engineering and 3D cell culture. Methods Mol Biol. 2011; 695:17-39).

Abdominal wall defects involve significant tissue loss, often requiring surgical reconstruction. Autologous flaps are scant, demand prolonged transfer surgery, and induce donor-site morbidity.

SUMMARY OF THE INVENTION

In one embodiment, the present invention provides an implant comprising: (a) an engineered tissue; and (b) a vasculature, wherein the engineered tissue comprises a porous scaffold embedded with cells comprising an endothelial cell, a fibroblast, a myoblast, a mesenchymal cell, an adipocyte or any combination thereof, wherein the vasculature feeds said cells. In another embodiment, the present invention further provides that the porous scaffold comprises poly-l-lactic acid (PLLA) and polylactic-co-glycolic-acid (PLGA). In another embodiment, the present invention further provides that the vasculature comprises a vein and an artery. In another embodiment, the present invention further provides that the vasculature is autologous. In another embodiment, the present invention further provides that the implant is configured to repair a large soft tissue defect such as but not limited to a full-thickness abdominal wall defect or a large skin defect.

In another embodiment, the present invention further provides a method for treating a subject afflicted with a large soft tissue defect, comprising implanting to a site of the large soft tissue defect an implant comprising: (a) an engineered tissue; and (b) a vasculature, wherein the engineered tissue comprises a porous scaffold embedded with cells comprising an endothelial cell, a fibroblast, a myoblast, a mesenchymal cell, an adipocyte or any combination thereof, wherein the vasculature feeds the cells, thereby treating a subject afflicted with a large soft tissue defect.

In another embodiment, the present invention further provides a process for making an implant comprising: (a) an engineered tissue; and (b) a vasculature, wherein said engineered tissue comprises a porous scaffold embedded with cells comprising an endothelial cell, a fibroblast, a myoblast, a mesenchymal cell, an adipocyte or any combination thereof, wherein said vasculature feeds said cells, comprising the steps of: (a) embedding the engineered tissue with said cells; (b) transplanting said porous scaffold embedded with cells under an Arteriovenous (AV) bundle; (c) removing said porous scaffold embedded with cells further comprising said vasculature derived from said AV bundle; and (d) removing said porous scaffold embedded with cells further comprising said vasculature derived from said AV bundle; thereby making an implant comprising: (a) an engineered tissue; and (b) a vasculature. In another embodiment, the present invention further provides that the porous scaffold embedded with cells remains under said AV bundle for 4 to 21 days. In another embodiment, the present invention further provides that the implant is configured to repair a large soft tissue defect such as but not limited to a full-thickness abdominal wall defect or a large skin defect (such as burns, cuts, etc.).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
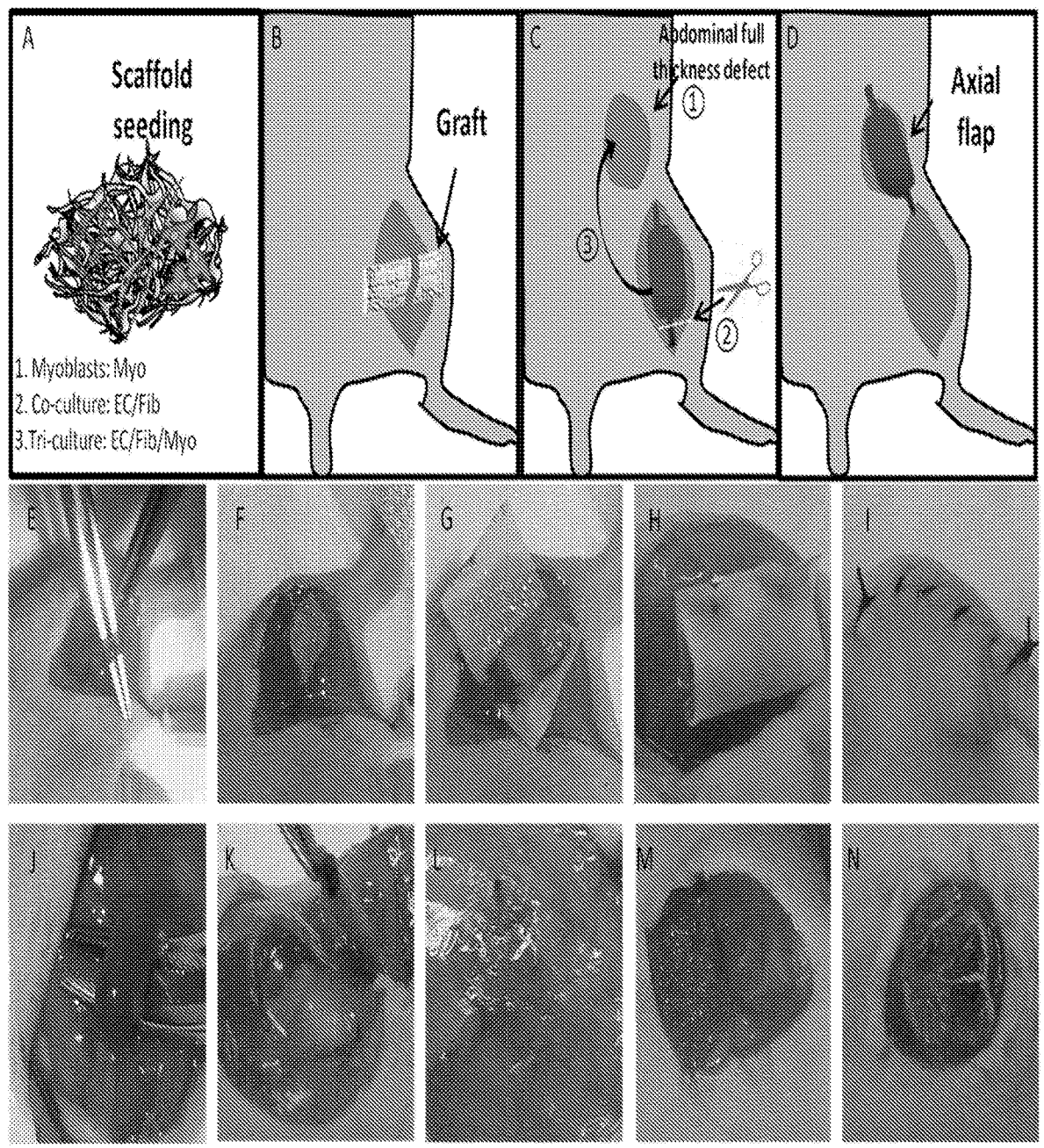
FIG. 1: Surgical implantation of fabricated tissue grafts, followed by flap transfer. (A-D) Schematic presentation of flap fabrication. (A) Cells were seeded within biodegradable ply-L-lactic-acid (PLLA)/poly-L-co-glycolic-acid (PLGA) scaffolds. (B) The fabricated tissue graft was folded around the blood vessels and sutured. (C-D) Transfer of the vascularized graft into the abdominal wall defect. (E) Isolation of the femoral artery and vein from the surrounding tissue. (F) The fabricated tissue graft was folded around the blood vessels and sutured. (G and H) The fabricated tissue graft was then separated from the skin and the surrounding tissue using a piece of sterile latex, which was then sutured. (I) Suturing of the overlying skin. (J) Representative image of a fabricated tissue graft one week after its implantation. (K) Transfer of the vascularized graft into the abdominal wall defect. (L) Appearance of the flap derived from cell-embedded scaffolds at one week after transfer; the flap is vascularized and viable. (M) Image of a piece of a cell-free scaffold applied to close the abdominal wall defect. (N) Appearance of a graft derived from a cell-free scaffold, one week after the transfer; the graft had become necrotic.

In one embodiment, the present invention provides an implant comprising: (a) an engineered tissue; and (b) a vasculature, wherein the engineered tissue comprises a porous scaffold embedded with cells comprising an endothelial cell, a fibroblast, a myoblast, a mesenchymal cell, an adipocyte or any combination thereof. In another embodiment, the present invention provides an implant comprising: (a) an engineered tissue; and (b) a vasculature, wherein the engineered tissue comprises a porous scaffold embedded with cells comprising an endothelial cell, a fibroblast, a myoblast, a mesenchymal cell, an adipocyte or any combination thereof wherein the vasculature feeds the cells. In another embodiment, the vasculature is functionally coupled to the scaffold. In another embodiment, the AV vasculature is grown on a scaffold populated with cells. In another embodiment, first the scaffold is populated with cells and then the AV vasculature is grown on the scaffold populated with cells. In another embodiment, the AV vasculature is functionally coupled to the scaffold's growing blood vessels derived from the endothelial cells (within the scaffold). In another embodiment, the growing blood vessels derived from the endothelial cells (within the scaffold) are connected to the AV vasculature is functionally coupled to the scaffold's.

In another embodiment, the present invention provides an engineered muscle flap bearing its own functional vascular pedicle for repair of a full-thickness abdominal wall defect. In another embodiment, the present invention provides a three-dimensional tissue graft constructed of a porous, biodegradable polymer scaffold embedded with endothelial cells, fibroblasts, a mesenchymal cell, an adipocyte, myoblasts, or any combination thereof and cultured in vitro and then implanted around the femoral artery and veins, before being transferred, with its vascular pedicle to a full-thickness defect in the same individual. In another embodiment, the present invention provides that within one week of implantation, the implants described herein demonstrated, extensive functional vascular density and perfusion, and anastomosis with host vessels. Another embodiment, the present invention provides that at one-week post-transfer, the engineered tissue (such as muscle flaps, connective tissue flaps or combinations of muscle and connective tissue flap) flaps were highly vascularized, well integrated within the surrounding tissue, and featured sufficient mechanical strength to support the abdominal viscera.

In some embodiment, "engineered tissue" according to the invention comprises heterogeneous cell culture grown in more than one layer. In some embodiment, "engineered tissue" according to the invention comprises heterogeneous cell culture wherein different cells interact.

In another embodiment, the present invention provides that the implant is an engineered muscle and/or adipose and/or skin flap. In another embodiment, the present invention provides that the vasculature is a vascular pedicle. In another embodiment, the present invention provides that the vasculature is an autologous vascular pedicle. In another embodiment, the present invention provides that the implant is an engineered muscle flap for reconstructing large defects, thereby circumventing both the need for autologous flaps and postoperative scarification. In another embodiment, the present invention provides that the implant is an engineered adipose and/or skin flap.

In another embodiment, the present invention provides that large defects are defects characterized by at least partial tissue lost. In another embodiment, the present invention provides large defects are defects that cannot before the de-novo growth of blood vessels within the boundaries of the defect. In another embodiment, large defects are soft-tissue defects. In another embodiment, the present invention provides that large defects are characterized by the immediate need of soft tissue coverage. In another embodiment, large defects are defects characterized by defects that impacts skin, connective tissue and vascular structures. In another embodiment, large defects are defects characterized by defects that impacts skin, connective tissue and vascular structures, nerves, and bones. In another embodiment, large defects are defects characterized by defects that impacts skin, tendons, connective tissue and vascular structures. In another embodiment, untreated large defects result in infection and further tissue loss.

In another embodiment, the scaffold is a soft engineered tissue comprising fibroblasts. In another embodiment, the scaffold is a soft engineered tissue comprising endothelial cells and fibroblasts. In another embodiment, the scaffold is a soft engineered tissue comprising myoblasts and fibroblasts. In another embodiment, the scaffold is a soft engineered tissue comprising endothelial cells and myoblasts. In another embodiment, the scaffold is a soft engineered tissue comprising endothelial cells, fibroblasts and epithelial cells.

In another embodiment, the scaffold is a soft engineered tissue comprising epithelial cells. In another embodiment, the scaffold is a soft engineered tissue comprising endothelial cells and epithelial cells. In another embodiment, the scaffold is a soft engineered tissue comprising myoblasts and epithelial cells. In another embodiment, the scaffold is a soft engineered tissue comprising endothelial cells and myoblasts. In another embodiment, the scaffold is a soft engineered tissue comprising endothelial cells, epithelial cells and epithelial cells. In another embodiment, "engineered tissue" is a "tissue scaffold". In another embodiment, the terms "engineered tissue" and "tissue scaffold" are interchangeable. In another embodiment, a "tissue scaffold" comprises a scaffold and cells seeded within the scaffold. In another embodiment, a scaffold is an inorganic scaffold.

In another embodiment, the scaffold is a soft engineered tissue comprising a mesenchymal cell. In another embodiment, the scaffold is a soft engineered tissue comprising a mesenchymal cell and an endothelial cell. In another embodiment, the scaffold is a soft engineered tissue comprising a mesenchymal cell and an epithelial cell. In another embodiment, the scaffold is a soft engineered tissue comprising a mesenchymal cell, an epithelial cell and a muscle cell.

In another embodiment, the scaffold is a soft engineered tissue comprising an adipocyte. In another embodiment, the scaffold is a soft engineered tissue comprising an adipocyte and an endothelial cell. In another embodiment, the scaffold is a soft engineered tissue comprising an adipocyte and a fibroblast. In another embodiment, the scaffold is a soft engineered tissue comprising an adipocyte, an epithelial cell and an endothelial cell.

In another embodiment, a large defect is a large soft tissue defect such as a full-thickness abdominal wall defect. In another embodiment, a large soft tissue defect or a full-thickness abdominal wall defect is the consequence of a radical oncological resection. In another embodiment, a full-thickness abdominal wall defect is an upper central trunk defect. In another embodiment, a large soft tissue defect or a full-thickness abdominal wall defect is an upper central trunk defect following radical tumor ablation. In another embodiment, a large defect is characterized by severe damage of local tissues where pedicled flaps have insufficient size or reach. In another embodiment, an implant of the invention solves the devastating consequences of total flap failure.

In another embodiment, the present invention provides that large defects are larger than 1 cm$^3$. In another embodiment, the present invention provides that large defects are larger than 2 cm$^3$. In another embodiment, the present invention provides that large defects are larger than 3 cm$^3$. In another embodiment, the present invention provides that large defects are larger than 5 cm$^3$. In another embodiment, the present invention provides that large defects are larger than 10 cm$^3$. In another embodiment, the present invention provides that large defects are larger than 12 cm$^3$. In another embodiment, the present invention provides that large defects are larger than 20 cm$^3$. In another embodiment, the present invention provides that large defects are larger than 40 cm$^3$.

In another embodiment, the present invention provides that large defects are 2 to 20 cm$^3$. In another embodiment, the present invention provides that large defects are 5 to 30 cm$^3$. In another embodiment, the present invention provides that large defects are 10 to 50 cm$^3$. In another embodiment, the present invention provides that large defects are larger than 2 to 20 cm$^3$. In another embodiment, the present invention provides that large defects are 5 to 30 cm$^3$. In another embodiment, the present invention provides that large defects are 20 to 80 cm$^3$. In another embodiment, the present invention provides that large defects are 2 to 20 cm$^3$. In another embodiment, the present invention provides that large defects are 5 to 30 cm$^3$. In another embodiment, the present invention provides that large defects are 15 to 150 cm$^3$.

In another embodiment, large defects are near anatomic free margins or crossing anatomic units present. In another embodiment, large defects have distorted anatomic free margins or landmarks. In another embodiment, large defects have limited local tissue supply.

In another embodiment, the present invention provides that the implant provides and/or induces the three-dimensional restoration of all missing components within the defect. In another embodiment, the present invention provides that the implant provides superior tissue for color and contour restoration. In another embodiment, the present invention provides that the implant of the invention is utilized in regional reconstruction. In another embodiment, the present invention provides that the implant of the invention is used to resurface the defect. In another embodiment, the present invention provides that the implant supplies a healthy, vascularized tissue thereby avoiding tissue necrosis within the defects or the defect's surroundings.

In another embodiment, the present invention provides that the implant is utilized for the reconstruction of large defects that cannot be closed locally and that have unfavorable wound conditions as severe infection, exposed sinuses, dura or brain tissue, CSF leakage or radiation damage.

In another embodiment, the present invention provides that the implant of the invention is superior to known pedicled flaps as is provides a more robust vascular supply to the wound. In another embodiment, the present invention provides that the implant of the invention supply the defect with a proliferating and a differentiating muscle tissue. In another embodiment, the present invention provides that the implant of the invention supply the defect with a proliferating and a differentiating muscle skin or cutaneous tissue. In another embodiment, the present invention provides that the implant of the invention supply the defect with a proliferating and a differentiating myocutaneous tissue. In another embodiment, the tissue or cells within the implant is/are vascularized prior to transplantation within the damaged tissue-defect. In another embodiment, the present invention provides that the scaffold of the implant of the invention comprises cells mimicking the composition of the desired tissue (the defect to be reconstructed).

In another embodiment, the present invention provides that the implant of the invention is materially different from previous flaps which do not include a scaffold that harbor cells. In another embodiment, the present invention provides that the implant of the invention is better vascularized, perfused and integrated with the surrounding tissue compared to previous flaps and scaffolds (free of cells but with the vasculature of an arteriovenous (AV) shunt). In another embodiment, the present invention provides that the implant of the invention is pedicled\axial flap. In another embodiment, the present invention provides that the implant of the invention comprises AV femoral blood vessels as pedicle.

In another embodiment, the scaffold is a porous sponge. In another embodiment, the present invention comprises an implant as described herein and cell culture medium. In another embodiment, the porous sponge comprises poly-l-lactic acid (PLLA) and polylactic-co-glycolic-acid (PLGA). In another embodiment, the present invention provides that the porous sponge provides a 3D tissue culture scaffold.

In another embodiment, the scaffold described herein comprises both poly-l-lactic acid (PLLA) and polylactic-co-glycolic-acid (PLGA). In another embodiment, the scaffold described herein comprises both poly-l-lactic acid (PLLA) and polylactic-co-glycolic-acid (PLGA). In another embodiment, PLLA and PLGA are in 1:3 to 3:1 w/w ratio. In another embodiment, PLLA and PLGA are in 1:2 to 2:1 w/w ratio. In another embodiment, PLLA and PLGA are in 1:1.5 to 1.5:1 w/w ratio. In another embodiment, PLLA and PLGA are in 1:1 w/w ratio.

In another embodiment, the present invention provides that the scaffold is a bioactive scaffold such that the bioactive scaffold controls the growth of the cells within the scaffold and the AV surrounding it. In another embodiment, the present invention provides a bioactive scaffold further supports de-novo, in-vivo tissue growth and vascularization at a site of implantation.

In another embodiment, the sponge is devoid of an organized structure, layer, or network of layers. In another embodiment, a porous sponge comprises at least 50% porosity. In another embodiment, a porous sponge comprises at least 60% porosity. In another embodiment, a porous sponge comprises at least 70% porosity. In another embodiment, a porous sponge comprises at least 75% porosity. In another embodiment, a porous sponge comprises at least 80% porosity. In another embodiment, a porous sponge comprises at least 85% porosity. In another embodiment, a porous sponge comprises at least 90% porosity. In another embodiment, a porous sponge comprises at least 92% porosity. In another embodiment, a porous sponge comprises at least 95% porosity.

In another embodiment, a porous sponge comprises pores having a diameter of at least 100 μm. In another embodiment, a porous sponge comprises pores having a diameter of at least 120 μm. In another embodiment, a porous sponge comprises pores having a diameter of at least 150 μm. In another embodiment, a porous sponge comprises pores having a diameter of 100-900 µm. In another embodiment, a porous sponge comprises pores having a diameter of 120-900 µm. In another embodiment, a porous sponge comprises pores having a diameter of 120-850 µm. In another embodiment, a porous sponge comprises pores having a diameter of 150-800 µm. In another embodiment, a porous sponge comprises pores having a diameter of 200-800 µm. In another embodiment, a porous sponge comprises pores having a diameter of 220-750 µm.

In another embodiment, cells are autogeneic cells. In another embodiment, cells are syngeneic cells. In another embodiment, cells are allogeneic cells. In another embodiment, cells care derived from different sources.

In another embodiment, the vasculature is autogeneic. In another embodiment, the vasculature is syngeneic. In another embodiment, the vasculature is allogeneic cells.

In another embodiment, the cells are cultured within the scaffold for at least 5 days. In another embodiment, the cells are cultured within the scaffold for at least 7 days. In another embodiment, the cells are cultured within the scaffold for at least 10 days. In another embodiment, the cells are cultured within the scaffold for at least 12 days. In another embodiment, the cells are cultured within the scaffold for at least 14 days.

In another embodiment, the endothelial cells are autologous. In another embodiment, the fibroblasts are autologous. In another embodiment, the endothelial cells are autologous. In another embodiment, the myoblasts are autologous. In another embodiment, the endothelial cells are autologous. In another embodiment, the mesenchymal cell is autologous. In another embodiment, the adipocyte is autologous.

In another embodiment, the mesenchymal cell is a stem cell. In another embodiment, mesenchymal cell, fibroblast or both are referred to as a "connective tissue cell". In another embodiment, the mesenchymal cell, fibroblast or both are CD73 and CD105 positive cells. In another embodiment, the mesenchymal cell, fibroblast or both are CD73, CD44 and CD105 positive cells. In another embodiment, the mesenchymal cell, fibroblast or both are CD73, CD43 and CD105 positive cells. In another embodiment, the mesenchymal cell, fibroblast or both are CD73, CD4, CD44 and CD105 positive cells.

In another embodiment, an engineered tissue of the invention comprises connective tissue. In another embodiment, an engineered tissue of the invention comprises connective tissue and muscle. In another embodiment, an engineered tissue of the invention comprises connective tissue. In another embodiment, an engineered tissue of the invention comprises muscle. In another embodiment, an engineered tissue of the invention comprises fat tissue.

In another embodiment, an engineered tissue of the invention comprises endothelial cell. In another embodiment, an engineered tissue comprises endothelial cells and connective tissue cells in a ratio of 2:1 to 20:1. In another embodiment, an engineered tissue comprises endothelial cells and connective tissue cells in a ratio of 2:1 to 10:1. In another embodiment, an engineered tissue comprises endothelial cells and connective tissue cells in a ratio of 4:1 to 20:1. In another embodiment, an engineered tissue comprises endothelial cells and muscle cells in a ratio of 2:1 to 20:1. In another embodiment, an engineered tissue comprises endothelial cells and muscle cells in a ratio of 2:1 to 10:1. In another embodiment, an engineered tissue comprises endothelial cells and muscle cells in a ratio of 4:1 to 20:1.

In another embodiment, myoblasts include satellite cells. In another embodiment, the composition described herein further comprises endothelial cells such as human umbilical vein endothelial cells (HUVEC), fibroblasts such as human foreskin fibroblasts (HFF) or both. In another embodiment, HUVEC and/or HFF are attached to the scaffold. In another embodiment, endothelial cells, fibroblast and myoblast or any other cell within the scaffold is a progenitor cell (such as a progenitor endothelial cell, a progenitor epithelial cell, a progenitor muscle cell, a progenitor adipocyte etc.). In another embodiment, myoblast is C2C12 cell. In another embodiment, muscle cell is a smooth muscle cell. In another embodiment, muscle cell is a muscle fiber. In another embodiment, muscle cell is a cardiac muscle cell. In another embodiment, muscle cell is a skeletal muscle cell. In another embodiment, a mesenchymal cell is a mesenchymal stem cell. In another embodiment, a mesenchymal cell of the invention is capable of differentiating into a lymphatic cell. In another embodiment, a mesenchymal cell of the invention is capable of differentiating into a blood cell. In another embodiment, a mesenchymal cell of the invention is capable of differentiating into a connective tissue cell. In another embodiment, a mesenchymal cell of the invention is capable of differentiating into an osteoblasts or an osteoclast. In another embodiment, a mesenchymal cell of the invention is capable of differentiating into a chondrocyte or a chondroblast.

In another embodiment, following the initial cultivation and growth of cells on the scaffold, an AV vasculature network is grown on the cell cultivated scaffold. In another embodiment, an AV vasculature network is grown on the cell cultivated scaffold by implanting the cell cultivated scaffold within an AV site of the same subject/individual destined to receive the implant of the invention. In another embodiment, the AV of the implant is autologous.

In another embodiment, a cell is attached to a scaffold such as described herein for at least 3 days. In another embodiment, a cell is attached to a scaffold such as described herein for at least 5 days. In another embodiment, a cell is attached to a scaffold such as described herein for at least 7 days. In another embodiment, a cell is attached to a scaffold such as described herein for at least 10 days. In another embodiment, a cell is attached to a scaffold such as described herein for at least 14 days. In another embodiment, a cell is attached to a scaffold such as described herein for 10 to 21 days. In another embodiment, a cell is attached to a scaffold such as described herein for 14 to 31 days. In another embodiment, an olfactory bulb cell is attached to a scaffold for at least 14 days.

In another embodiment, a porous sponge-scaffold of the invention is further coated with a polymer. In another embodiment, a porous sponge-scaffold of the invention is further coated with an extracellular matrix protein. In another embodiment, a porous sponge-scaffold of the invention is further coated with fibronectin. In another embodiment, a porous sponge-scaffold of the invention is further coated with polypyrrole. In another embodiment, a porous sponge-scaffold of the invention is further coated with polycaprolactone. In another embodiment, a porous sponge-scaffold of the invention is further coated with poly(ethersulfone). In another embodiment, a porous sponge-scaffold of the invention is further coated with poly(acrylonitrile-co-methylacrylate) (PAN-MA). In another embodiment, a porous sponge-scaffold of the invention further comprises a chemoattractant such as but not limited to laminin-1.

In another embodiment, a composition as described herein further comprises fibrin. In another embodiment, a composition as described herein further comprises thrombin.

In another embodiment, a scaffold such as described herein is 10-160 mm³. In another embodiment, a scaffold such as described herein is 10-80 mm³. In another embodiment, a scaffold such as described herein is 15-150 mm³. In another embodiment, a scaffold such as described herein is a square. In another embodiment, a scaffold such as described herein is a rectangle. In another embodiment, a scaffold such as described herein is 8-100 cm³. In another embodiment, a scaffold such as described herein is 10-90 cm³.

In another embodiment, the three three-dimensional scaffolds described herein can further include a therapeutic agent. In another embodiment, the therapeutic agent can be any therapeutic agent. In another embodiment, the therapeutic agent can be a polypeptide, polypeptide fragment, nucleic acid molecule, small molecule, ribozyme, shRNA, RNAi, antibody, antibody fragment, scFv, enzyme, carbohydrate, or any combination thereof. In some embodiments, the therapeutic agent can be brain-derived neurotrophic factor (BDNF), neurotrophic 3 (NT3), nerve growth factor (NGF), or glial cell-line derived neurotrophic factor (GNDF). The therapeutic agent, in some embodiments, is chondroitinase ABC (chABC) or sialidase. The three-dimensional scaffold can release, in one embodiment, the therapeutic agent for at least 1 day, 1 week, or 1 month.

In another embodiment, the scaffold includes a cellular substrate. In another embodiment, the cellular substrate is any cellular substrate.

In another embodiment, a composition as described herein further comprises a material selected from the group consisting of collagen-GAG, collagen, fibrin, PLA, PGA, PLA-PGA co-polymer, poly(anhydride), poly(hydroxy acid), poly(ortho ester), poly(propylfumerate), poly(caprolactone), polyamide, polyamino acid, polyacetal, biodegradable polycyanoacrylate, biodegradable polyurethane and polysaccharide, polypyrrole, polyaniline, polythiophene, polystyrene, polyester, nonbiodegradable polyurethane, polyurea, poly(ethylene vinyl acetate), polypropylene, polymethacrylate, polyethylene, polycarbonate and poly(ethylene oxide).

In another embodiment, a composition as described herein is cultured for at least 14 days in-vitro, in order to reach baseline proliferation rates.

In another embodiment, a composition as described herein further comprises a cell adhesion promoting agent, a proliferation inducer, a differentiation inducer, an extravasation inducer and/or a migration inducer. In another embodiment, a composition as described herein further comprises a cell adhesion protein, a growth factor, a cytokine, a hormone, a protease a protease substrate, or any combination thereof. In another embodiment, any substance as described herein is attached to the scaffold. In another embodiment, any substance as described herein is embedded within the scaffold. In another embodiment, any substance as described herein is impregnated within the scaffold. In another embodiment, a scaffold such as described herein is coated with a gel. In another embodiment, a scaffold such as described herein is biodegradable.

In another embodiment, the porosity of the scaffold is controlled by a variety of techniques known to those skilled in the art. In another embodiment, as the porosity is increased, use of polymers having a higher modulus, addition of suffer polymers as a co-polymer or mixture, or an increase in the cross-link density of the polymer are used to increase the stability of the scaffold with respect to cellular contraction.

In another embodiment, the choice of polymer and the ratio of polymers in a co-polymer scaffold of the invention is adjusted to optimize the stiffness/porosity of the scaffold. In another embodiment, the molecular weight and cross-link density of the scaffold is regulated to control both the mechanical properties of the scaffold and the degradation rate (for degradable scaffolds). In another embodiment, the mechanical properties are optimized to mimic those of the tissue at the implant site. In another embodiment, the shape and size of the final scaffold are adapted for the implant site and tissue type. In another embodiment, scaffold materials comprise natural or synthetic organic polymers that can be gelled, or polymerized or solidified (e.g., by aggregation, coagulation, hydrophobic interactions, or cross-linking) into a 3-D open-lattice structure that entraps water and/or other molecules, e.g., to form a hydrogel.

In another embodiment, polymers used in scaffold material compositions are biocompatible, biodegradable and/or bioerodible and act as adhesive substrates for cells. In another embodiment, the structural scaffold materials are non-resorbing or non-biodegradable polymers or materials. The phrase "non-biodegradable polymer", as used herein, refers to a polymer or polymers which at least substantially (i.e. more than 50%) do not degrade or erode in-vivo. The terms "non-biodegradable" and "non-resorbing" are equivalent and are used interchangeably herein.

In another embodiment, the phrase "biodegradable polymer" as used herein, refers to a polymer or polymers which degrade in-vivo, and wherein erosion of the polymer or polymers over time occurs concurrent with or subsequent to release of cells/tissue. The terms "biodegradable" and "bioerodible" are equivalent and are used interchangeably herein.

In another embodiment, scaffold materials comprise naturally occurring substances, such as, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units. In another embodiment, structural scaffold materials are ionic hydrogels, for example, ionic polysaccharides, such as alginates or chitosan. Ionic hydrogels may be produced by cross-linking the anionic salt of alginic acid, a carbohydrate polymer isolated from seaweed, with ions, such as calcium cations.

In another embodiment, the scaffolds of the invention are made by any of a variety of techniques known to those skilled in the art. Salt-leaching, porogens, solid-liquid phase separation (sometimes termed freeze-drying), and phase inversion fabrication are used, in some embodiments, to produce porous scaffolds.

As used herein, "transplanting" refers to providing the scaffold supported cells of the present invention, using any suitable route. Typically, the scaffold supported cells are administered by injection using a catheter.

In another embodiment, a culture medium comprises DMEM/F12, Nutrient Mix and 7-15% fetal bovine serum. In another embodiment, a culture medium comprises Neurobasal-A (Invitrogen). In another embodiment, a culture medium comprises 0.5-1.2 mM L-glutamine. In another embodiment, a culture medium comprises 0.1-0.8% methylcellulose. In another embodiment, a culture medium comprises 5-15 mM HEPES. In another embodiment, a culture medium has a pH of 7.2-7.8. In another embodiment, a culture medium has a pH of 7.4-7.6. In another embodiment, a culture medium comprises 2-8 µg/ml Gentamycin. In another embodiment, a culture medium comprises B27- supplement. In another embodiment, a culture medium comprises L-15 medium (Invitrogen). In another embodiment, a culture medium is any medium provided in: Ronald Doucette. Protocols for Neural Cell Culture (2001) which is incorporated herein by reference in its entirety. In another embodiment, a culture medium is any medium provided in: Doucette, 1984, Doucette, 1986, 11,1; Raisman, 1985; Li et al., 1997; Perez-Bouza et al., 1998; Ramon-Cueto and Nieto-Sampedro, 1994; Ramon-Cueto et al., 1998; Smale et al., 1996; Franklin et al., 1996; Imaizumi et al., 1998; Doucette, 1990; Doucette, 1995; Franklin and Barnett, 1997; Ramon-Cueto and Avila, 1998; Ramon-Cueto and Valverde, 1995 which are incorporated herein by reference in their entireties.

In another embodiment, the present invention provided that OB-derived cells promotes the formation of dense, HUVEC-rich networks of thin vessel-like structures on scaffolds that are furthered integrated fused with the AV vasculature, further highlighting the supportive features of the implant of the invention for injury repair.

In another embodiment, the present invention further provides a method for vascularizing a scaffold of the invention for obtaining an implant as described herein. In another embodiment, 3D scaffolds of the invention maintained and strengthened the unique therapeutic properties of the embedded cells. In another embodiment, 3D scaffolds of the invention are further supported by the AV vasculature. In another embodiment, the phrase "supported by the AV vasculature" includes feeding the cells of the present invention embedded within the scaffold as described herein by the autologous AV vasculature of the invention. In another embodiment, vasculature comprises both a vein and an artery.

In another embodiment, the present invention further provides a method for treating a subject afflicted with a large soft tissue defect, comprising implanting to a site of a large soft tissue defect an implant comprising: (a) an engineered tissue; and (b) a vasculature, wherein said engineered tissue comprises a porous scaffold embedded with cells comprising an endothelial cell, a fibroblast, a myoblast, an adipocyte, a mesenchymal cell or any combination thereof, wherein the vasculature feeds the cells, thereby treating a subject afflicted with a large soft tissue defect.

In another embodiment, the invention provides a regenerative cell population containing at least one regenerative cell that when deposited on a scaffold as described herein and implanted into a subject in need, provides a regenerative effect for the damaged tissue or tissues that is the subject of the reconstruction, repair, augmentation, or replacement contemplated herein. In another embodiment, the invention provides that the cells of the invention is a regenerative cell population that has the ability to stimulate or initiate regeneration of vasculature, skin and muscle tissues upon implantation into a patient in need. In general, the regeneration of an organ or tissue structure is characterized by the restoration of cellular components, tissue organization and architecture, function, and regulative development. In addition, the regenerative cell population grown on a scaffold as described herein minimizes the incompleteness or disorder that tends to occur at the implantation site. In another embodiment, disorganization at the site of implantation can manifest itself as increased collagen deposition and/or scar tissue formation, each of which can be minimized through the use of a composition as described herein.

In another embodiment, the present invention further provides a process for making an implant comprising: (a) an engineered tissue; and (b) a vasculature, wherein said engineered tissue comprises a porous scaffold embedded with cells comprising an endothelial cell, a fibroblast, a myoblast, an adipocyte, a mesenchymal cell or any combination thereof, wherein the vasculature feeds the cells, comprising the steps of: (a) embedding said engineered tissue with the cells; (b) transplanting the porous scaffold embedded with cells under an Arteriovenous (AV) bundle; and (c) removing the porous scaffold embedded with cells further comprising the vasculature derived from the AV bundle; thereby making an implant comprising: (a) an engineered tissue; and (b) a vasculature.

In another embodiment, the porous scaffold embedded with cells remains under the AV bundle for 4 to 21 days. In another embodiment, the porous scaffold embedded with cells remains under the AV bundle for 7 to 30 days. In another embodiment, the porous scaffold embedded with cells remains under the AV bundle for 10 to 31 days. In another embodiment, the porous scaffold embedded with cells remains under the AV bundle for 7 to 21 days.

Figure 6:
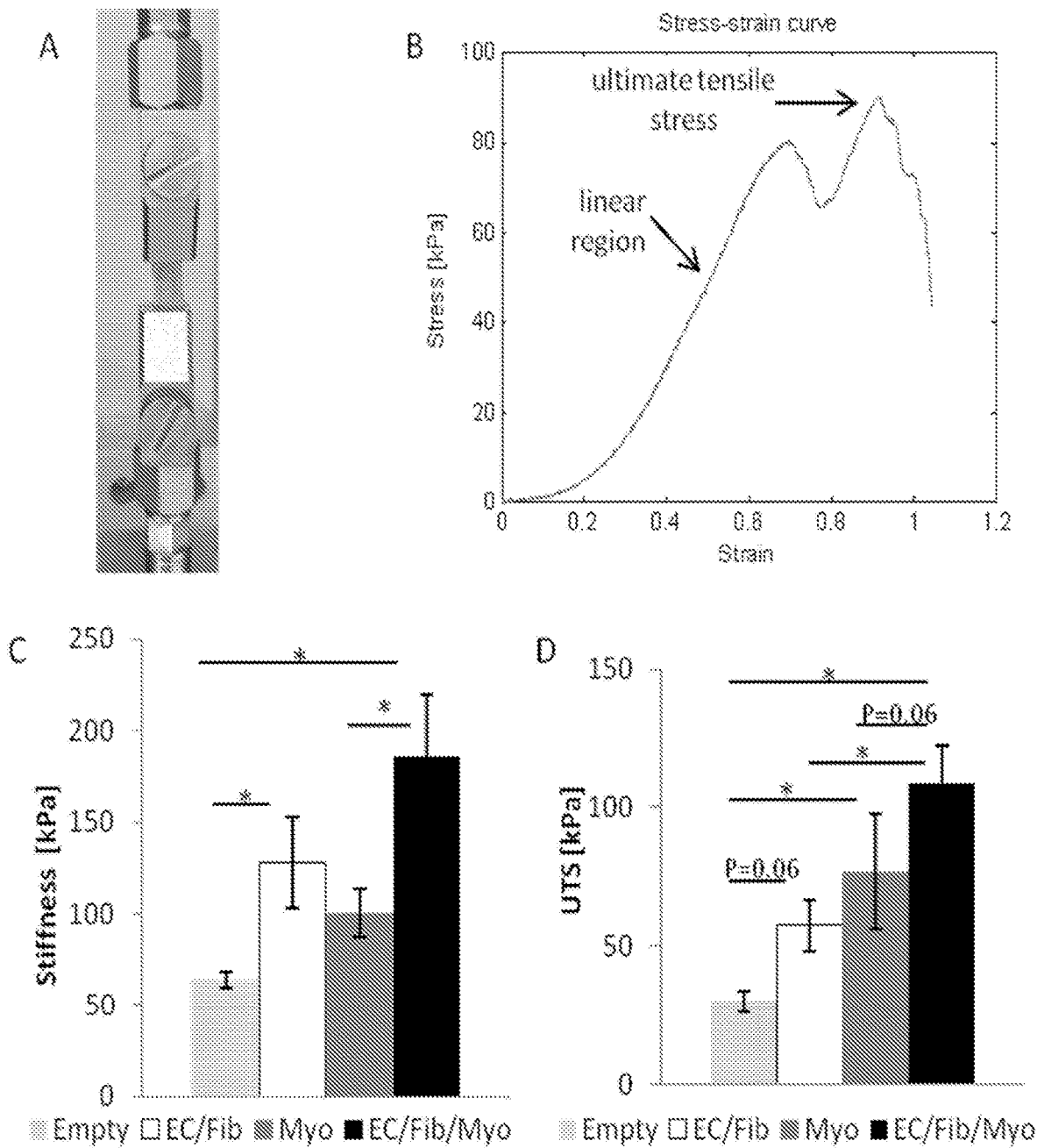
FIG. 6: Mechanical properties of flaps one week after transfer. (A) Schematic diagram of a flap being stretched in the Biodynamic test instrument (Bose Corporation, MN, USA) (B) A typical stress-strain curve. The linear region of the stress-strain curve was used to calculate flap stiffness (C) and the maximum point of the curve was deemed the ultimate tensile strength (UTS) of the flaps (D). *=p<0.05 according to the results of the one-way analysis of variance and the post-hoc Student-Newman-Keuls multiple comparisons test. For all determinations, the sample size was n=3 and all values are represented as mean±standard error of the mean.

In another embodiment, cells are grown on the scaffold which is then implanted within an AV site of the patient (the implant recipient). In another embodiment, flap is formed within the patient (in-vivo), autologous donor body. In another embodiment, flap extraction within one-week post transfer, was fully functional and demonstrated firm attachment to the surrounding tissue. In another embodiment, the implant of the invention has a better tensile strength than a flap free of cells or a scaffold with cells burt free of AV (FIG. 6A-B). In another embodiment, the present invention provides, a novel method for repair of a large soft tissue defect, using an engineered tissue-based flap. In another embodiment, the prefabricated graft was implanted around the AV and isolated from its suroundings. In another embodiment, the implant (synonymous with graft and flap) proved viable, vascularized, and perfused, and contained blood vessels which anastomosed with host blood vessels. In another embodiment, following transfer of the implant to a full-thickness defect, the implant remained viable, vascularized, and became well integrated within the surrounding tissue. In another embodiment, the cell types integrated in the engineered flaps dictate its mechanical strength.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the singular forms "a", "an", and "the" include plural forms unless the context clearly dictates otherwise. Thus, for example, reference to "a therapeutic agent" includes reference to more than one therapeutic agent.

Unless specifically stated or obvious from context, as used herein, the term "or" is understood to be inclusive.

The term "including" is used herein to mean, and is used interchangeably with, the phrase "including but not limited to".

As used herein, the terms "comprises," "comprising," "containing," "having" and the like can have the meaning ascribed to them in U.S. patent law and can mean "includes," "including," and the like; "consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the term "therapeutically active molecule" or "therapeutic agent" means a molecule, group of molecules, complex or substance administered to an organism for diagnostic, therapeutic, preventative medical, or veterinary purposes. This term includes pharmaceuticals, e.g., small molecules, treatments, remedies, biologics, devices, and diagnostics, including preparations useful in clinical screening, prevention, prophylaxis, healing, imaging, therapy, surgery, monitoring, and the like. This term can also specifically include nucleic acids and compounds comprising nucleic acids that produce a bioactive effect, for example.

In some embodiments, a composition of the invention comprises pharmaceutically active agents. In some embodiments, pharmaceutically active agents are added prior to transplantation. Pharmaceutically active agents include but are not limited to any of the specific examples disclosed herein. Those of ordinary skill in the art will recognize also numerous other compounds that fall within this category and are useful according to the invention. Examples include a growth factor, e.g., nerve growth factor (NGF), brain-derived neurotrophic factor (BDNF), neurotrophic 3 (NT3), or glial cell-line derived neurotrophic factor (GNDF), a steroid, an anti-inflammatory agent, an analgesic agent, a sedative, a peptidic agent, a biopolymeric agent, an antimicrobial agent, an enzyme (e.g., chondroitinase ABC (chABC) or sialidase), a protein, or a nucleic acid. In a further aspect, the pharmaceutically active agent can be steroids such as betamethasone, dexamethasone, methylprednisolone, prednisolone, prednisone, triamcinolone, budesonide, hydrocortisone, and pharmaceutically acceptable hydrocortisone derivatives; non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam, celocoxib, refocoxib, and N-[2-(cyclohexyloxy)-4-nitrophenyl]methanesulfonamide; analgesic agents such as salicylates; sedatives such as benzodiazapines and barbiturates; antimicrobial agents such as penicillins, cephalosporins, and macrolides, including tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, minocycline, doxycycline, vancomycin, kanamycin, cephalosporins such as cephalothin, cephapirin, cefazolin, cephalexin, cephardine, cefadroxil, cefamandole, cefoxitin, cefaclor, cefuroxime, cefonicid, ceforanide, cefitaxime, moxalactam, cetizoxime, ceftriaxone, cefoperazone; nucleic acids such as DNA sequences encoding for biological proteins and antisense oligonucleotides; and other pharmacological agents that have been shown to promote axonal regeneration such as paclitaxel (TAXOL®). The term also refers to combinations of any of the therapeutic agents disclosed herein.

As used herein, the term "biological agent," "biological molecule," or "biological therapeutic" is intended to mean a subset of therapeutic agents that are a polypeptide or nucleic acid molecule. In specific embodiments, the biological therapeutic is an agent that induces or enhances nerve growth, e.g., a neurotrophic agent. Examples of useful neurotrophic agents are ocFGF (acidic fibroblast growth factor), FGF (basic FGF), NGF (nerve growth factor), BDNF (brain derived neurotrophic factor), CNTF (ciliary neurotrophic factor), MNGF (motor nerve growth factor), NT-3 (neurotrophin-3), GDNF (glial cell line-derived neurotrophic factor), NT4/5 (neurotrophin4/5), CM101, HSP-27 (heat shock protein-27), IGF-I (insulinlike growth factor), IGF-II (insulin-like growth factor 2), PDGF (platelet derived growth factor) including PDGF-BB and PDGF-AB, ARIA (acetylcholine receptor inducing activity), LIF (leukemia inhibitory factor), VIP (vasoactive intestinal peptide), GGF (glial growth factor), and IL-1 (interleukin-1). In a preferred embodiment, the biological therapeutic is NGF or GNDF. In embodiments, the biological therapeutic is an antibody, antibody fragment, or scFV that induces or enhances nerve growth, e.g., an antibody specific for any of the neurotrophic agents described herein. In other embodiments, the biological therapeutic is a ribozyme, shRNA, or RNAi that induces or enhances nerve growth, e.g., an RNA molecule specific for any of the neurotrophic agents described herein.

As used herein, the term "scaffold" refers to a structure comprising a biocompatible material that provides a surface suitable for adherence/attachment, maturation, differentiation, and proliferation of cells. A scaffold may further provide mechanical stability and support. A scaffold may be in a particular shape or form so as to influence or delimit a three-dimensional shape or form assumed by a population of proliferating cells. All shapes are 3-dimensional and include: films, ribbons, cords, sheets, flat discs, cylinders, spheres, 3-dimensional amorphous shapes, etc.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymeric materials of the invention, biocompatible refers to the ability of the polymeric material (or polymeric materials) to be accepted by and to function in its intended manner in a recipient.

As used herein, "therapeutically effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with the transplantation procedure. A physician or veterinarian of ordinary skill can readily determine and prescribe the effective amount of the bioactive agent required.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Material and Methods

Cell Culture

Myoblasts (C2C12; American Type Culture Collection, VA, USA) were cultured in Dulbecco's minimal essential medium (DMEM; Gibco® Life Technologies), which was supplemented with 10% fetal bovine serum (FBS; HyClone, *Thermo Fisher Scientific, USA*), 2.5% HEPES buffer (Biological Industries, Israel), 100 U/ml penicillin, and 0.1 mg/ml streptomycin (Pen-Strep Solution, Biological Industries, Israel). Human umbilical vein endothelial cells (HUVEC; Lonza, USA) and red fluorescent protein (RFP)-expressing-HUVEC (HUVEC-RFP) (Angio-Proteomie, USA) were cultured in endothelial cell medium (EGM-2) and microvascular endothelial cell growth medium (EGM-MV), respectively, supplemented with the components of their respective bullet kits (Lonza, USA). Normal human dermal fibroblasts (NHDF; Lonza, USA) were cultured in DMEM, which was supplemented with 10% FBS, 1% nonessential amino acids (Biological Industries), 0.2% β-mercaptoethanol (Biological Industries), and Pen-Strep solution (Biological Industries). All incubations were performed in a 5% $CO_2$ humidified atmosphere at 37° C.

Graft Fabrication

Porous scaffolds were fabricated from 50% PLLA (Polysciences Inc., Warrington, Pa., USA) and 50% PLGA (Boehringer-Ingelheim) in accordance with a previously described protocol[40]. Three types of fabricated grafts were prepared, by embedding scaffolds with either (1) myoblasts (Myo graft), (2) HUVECs and NHDFs (EC/Fib graft), or (3) HUVECs, NHDFs, and myoblasts (EC/Fib/Myo graft), designed to most closely mimic the composition of a muscle tissue. For this purpose, three different cell suspensions were prepared [(a) $0.5 \times 10^6$ myoblasts in myoblast medium, (b) $0.9 \times 10^6$ HUVECs and $0.2 \times 10^6$ NHDFs in 1:1 HUVEC:NHDF medium, and (c) $0.5 \times 10^6$ myoblasts, $0.9 \times 10^6$ HUVECs, and $0.2 \times 10^6$ NHDFs in 1:1 HUVEC:myoblasts medium] by growing each cell type separately, in its respective medium, and preparing each suspension by suspending the cells in a mixture of 4 μl Matrigel and 4 μl culture medium. Each cell suspension was then seeded onto the scaffold, and allowed to solidify (30 minutes, 37° C., 5% $CO_2$) in a 6-well plate. After solidification, culture medium (4 ml) was added to each well and was replaced every other day for a period of ten days.

Graft Implantation

All animal studies were approved by the Committee on the Ethics of Animal Experiments of the Technion. For all animal-based determinations, athymic nude male mice (7-9-week-old, Harlan Laboratories Inc., Israel) were randomly assigned to three or four groups of 3-5 mice/group. Prior to graft (i.e. 10-day-old cell-populated scaffolds) implantation, mice were anesthetized by an intraperitoneal injection (35 μL/20 g) of a ketamine:xylazine (6:1) mixture.

The femoral AV bundle was then exposed from the level of the inguinal ligament to the knee area. In order to preserve the blood flow, the profunda was left untouched. The graft was folded around the exposed femoral AV, below the profunda and above the bifurcation to the tibial and proneal AV, and its ends joined using 8-0 silk sutures. In order to ensure implant vascularization by the femoral AV bundle only, a piece of sterilized latex was wrapped around the graft, and secured with 8-0 silk sutures. The overlying skin was then closed, using 4-0 silk sutures. All mice were monitored closely until they recovered from the anesthesia and every day thereafter, until the grafts were harvested for analysis or until they were transferred as flaps.

Flap Transfer

Mice were anesthetized with the ketamine:xylazine cocktail, 1-2 weeks after graft implantation. The tissue flap was then carefully dissected from the surrounding tissues, after removal of its latex cover. The distal ends of the femoral AV were ligated with 8-0 silk sutures and then cauterized at the level of the knee, distally to the folded implanted tissue. The femoral AV with the surrounding tissues was then transferred upwards, as a flap, to repair a full-thickness defect in the ventral abdominal wall, which was made, during the same procedure, by removing a 1.0×0.8 cm section of the rectus abdominus muscle, with the overlying skin. The flap was sutured to the surrounding muscle tissues, using 8-0 silk sutures, and the wound was covered with iodinated gauze and a sterile plaster. The skin of the leg was closed using 4-0 silk sutures. All mice were closely monitored every day, for one week, after which they were euthanized to allow for flap retrieval for tensile strength testing (see below) or for histological or immunohistological analysis.

Determination of the Extent of Functional Graft Vascularization

The extent of tissue graft vascularization was determined one and two weeks after implantation. Following anesthetization with ketamine:xylazine, 10 mg/ml fluorescein isothiocyanate-conjugated dextran (FITC-Dextran, Sigma-Aldrich) was intravenously injected into the tail vein. Upon completion of the injection, the mice were euthanized, and the graft was imaged using confocal microscopy. The grafts were then excised and transferred to 10% buffered formalin (Sigma-Aldrich) for histological or immunohistological analysis.

Vascularization was quantified using MATLAB (Mathworks, Mass., USA). First, the green channel (excitation=488 nm) of the confocal microscopic images was isolated. The resulting images were then passed through a high-pass filter in order to accentuate the high-contrast structures. Next, a despeckling filter was used to remove noise that might have been amplified by the high-pass filter. The resulting image was then thresholded, using a predefined value; the threshold value was adjusted so that the features and structures in the original image were visible in the binary image. A size threshold was then applied so that only groups of connected pixels larger than the size threshold remained in the binary image. Finally, the skeleton of the vessels in the graft was outlined using Zhang-Suen's algorithm in order to determine the functional vessel density (FVD) in each graft. The FVD was calculated by summing the lengths of the midline of each vessel and dividing the result by the area of the region of interest (ROI).

Ultrasound Determination of Vascular Perfusion of the Graft

Before transfer, vascular perfusion of the graft was measured one and two weeks after implantation, by ultrasonography. For this purpose, mice were anesthetized using 2% isoflurane; animal body temperature was maintained using a movable, heated stage (VisualSonics), whose temperature was set at 38° C. Patency of the femoral vessels was examined and the grafts were first located using B-mode and color Doppler ultrasonography (Supplementary 1), with an MS250 non-linear transducer (VisualSonics). Then the Vevo Micromarker non-targeted contrast agent (VisualSonics, (microbubbles)) was injected into the tail vein. Images were captured in the non-linear contrast mode of the Vevo 2100 high-resolution ultrasound system, and were analyzed using the Vevo 2100 software, as described previously[21]. Briefly, an ROI was drawn on the graft's image, which was obtained from B-mode and contrast-mode images that were captured immediately after a disruption pulse, which destroys all of the injected microbubbles. After the disruption pulse, the microbubbles re-fill the vessels at a rate that only depends on the flow rate of the microbubbles in the capillaries and is independent of the injection rate of the microbubbles. The peak enhancement (PE) is the ratio of the mean intensity of the non-linear signal after the injection of the microbubbles versus after the disruption pulse, and is a measure of the perfusion volume. The flow rate can be determined from the time (T) that elapses until the peak signal (P). Patency of the femoral vessels post-transfer was ensured using the Doppler mode. Immunohistological and histological staining of the grafts and flaps.

Grafts were fixed in 10% neutral buffered formalin (Sigma Aldrich), and embedded in paraffin using standard fixation and embedding procedures. The paraffin-embedded sections were then deparaffinized by immersion in 100% xylene and then rehydrated by serial immersions in decreasing concentrations of ethanol. Standard protocols were used for hematoxylin and eosin (H&E) and Masson Trichrome (MT) staining of the paraffin-embedded sections. For immunohistological staining, the epitopes were recovered by heating the specimens in Vector® antigen unmasking solution (Vector Labs). The activity of endogenous peroxidase was quenched by first incubating the slides in 3.3% $H_2O_2$ solution in methanol for ten minutes, rinsing in phosphate buffered saline (PBS), and then incubating in a 2% goat serum blocking solution, for 30 minutes at room temperature (RT). The slides were then incubated overnight, at 4° C., in an anti-CD31 antibody solution (1:50; Abcam), rinsed with PBS, incubated with a biotinylated secondary antibody (1:400; Vector Labs) for 30 minutes at RT, rinsed with PBS, and incubated with streptavidin-peroxidase (1:400; Vector Labs) for another 30 minutes at RT. The nuclei were stained in blue by immersing the sections in hematoxylin for two minutes. After gentle rinsing in water, the sections were covered with Vectamount™ mounting medium (Vector Laboratories, CA, USA). CD31 staining was visualized as a brown stain using the aminoethylcarbazole (AEC) substrate kit (Invitrogen). CD31 positive staining was determined and quantified in a double blind assay.

Preparation of Flaps for Immunofluorescence Analyses

The tissues were harvested and fixed in 4% paraformaldehyde (PFA; Electron

Microscopy Sciences, USA) for 1-2 hours, incubated overnight in a 30% (w/v) sucrose solution, embedded in optimal cutting temperature (OCT) compound (Tissue-Tec, USA), and frozen for subsequent cryosectioning (5-7 μm). The sections were incubated in a 0.5% Tween solution for 20 minutes, rinsed with PBS, and then blocked with a 5% (w/v) bovine serum albumin (BSA; Sigma-Aldrich) blocking solution for 30 minutes. The sections were then simultaneously incubated in an anti-CD31 antibody solution (1:200; BD Biosciences, USA) and an anti-desmin antibody solution (1:50; Santa Cruz Biotechnology, Inc., USA) for 30 minutes at RT before being thoroughly washed in PBS. The sections were then labeled with Alexa 488 and Alexa 532 dye conjugates of IgG (1:200; Jackson Immunoresearch Laboratories, Inc., PA, USA). The slides were then mounted in Vectashield that contained 4',6-diamidino-2-phenylindole (DAPI) (Vector Laboratories, CA, USA), before being examined under a fluorescence microscope (Axiovert 200M, Zeiss) and a Leica TCS-LSI confocal microscope.

Determination of the Extent of Flap Vascularization and Vessel Circumference

The extent of flap vascularization and vessel circumferences were determined by quantifying CD31 staining. For this purpose, flap cryo-sections were first immunostained for murine CD31 (mCD31), which was quantified using the tile function of the Leica TCS-LSI confocal microscope and a MATLAB code. The code first filtered the green (excitation=488 nm) channel from the image in order to isolate the mCD31 staining. An automatic image analysis process was then used to segment the blood capillaries in a given ROI and to calculate the area and circumference of the segmented vessels. The image segmentation was performed as follows: single images, taken from the TIF stack sequence input, which was created by the confocal microscope's software, were first summed. Median image filtration was then applied in order to reduce noise before manual masking of the ROI.

The resultant image was converted into a binary image, and Sobel edge filtering was applied in order to detect the edges of the capillaries. This image of the edges was segmented using morphological operators, which enhanced and connected the edges of the vessels. Dilation was used in order to intensify and connect the vessels, and a dilation operator was used to reduce noise and delete small pixel elements. The image, now showing only the intensified edges of the vessels, was analyzed using an 8-neighbor boundary detection algorithm that generated a single-vector graphics representation for each closed vessel. The area and circumference of each vessel were calculated and written into a CSV text file, which was used for the final analysis. In this analysis, vessels with small lumens (circumference<8 pixels) were categorized as noise and were disregarded in the final analysis.

Determination of the Extent of Vascular Anastomosis

In order to distinguish between host vessels and the implanted HUVECs, and to determine whether the vessels had anastomosed, a mixture of rhodamine-labeled *Ulex europaeus* agglutinin I (UEA; Vector Laboratories) human specific lectin and fluorescein isothiocyanate (FITC)-conjugated *Griffonia simplifolia* isolectin B4 (GS-IB4; Vector-Labs) murine specific lectin were injected into the tail vein, one week after graft implantation, using a previously described protocol[21]. Mice were euthanized 20 minutes after the injection and the grafts were harvested, fixed in 10% buffered formalin for 2-4 hours, incubated overnight in 30% (w/v) sucrose, embedded in OCT compound, frozen, and cryosectioned into 60-μm sections for confocal imaging.

Tensile Testing of the Flaps

A stress-strain curve was generated using the Biodynamic test instrument (Bose Corporation, MN, USA), under a strain rate of 0.01 mm/sec until failure. Stress was calculated as the measured force divided by the cross-sectional area of the flap and strain was calculated as elongation divided by the flap's initial length. The flap's stiffness was calculated as the slope of the linear region of the stress-strain curve and the maximum point of the curve was deemed to be the ultimate tensile strength (UTS)[31]. For these determinations, the flaps were retrieved seven days after transfer and their dimensions were obtained while they were maintained in PBS, and immediately after mounting them onto the system's grips.

Statistical Analysis

All data were statistically analyzed by a one-way analysis of variance (ANOVA), followed by a post-hoc Student-Newman-Keuls multiple comparisons test using a computerized statistical program (InStat, GraphPad Software, Inc. CA, USA). Statistical significance was set at 5% and all results are presented as mean±standard error of the mean (SEM).

Example 1

Analysis of Graft Integration and Vascularization

Postimplantational viability of a large and thick engineered tissue, requires nutritional support which can only be provided by a large blood vessel. For this purpose, grafts constructed of a porous, biodegradable PLLA/PLGA scaffold embedded with endothelial cells (ECs), fibroblasts, and/or myoblasts (FIG. 1A), were cultured for ten days and then folded around the host's AV while being separated from the surrounding tissue by a piece of sterile latex (FIG. 1B-E). One and two weeks postimplantation the graft with the AV were transferred towards the abdominal full-thickness wall defect as an axial flap (FIG. 1C-D and FIG. 1J-N).

Three types of fabricated grafts were prepared, consisting of either (1) myoblasts (Myo graft), (2) ECs and fibroblasts (EC/Fib graft), or (3) ECs, fibroblasts and myoblasts (EC/Fib/Myo graft), designed to most closely mimic the composition of a muscle tissue. An empty scaffold was used as a control. The viability and vascularization of the grafts were assessed one week and two weeks after implantation.

Figure 2:
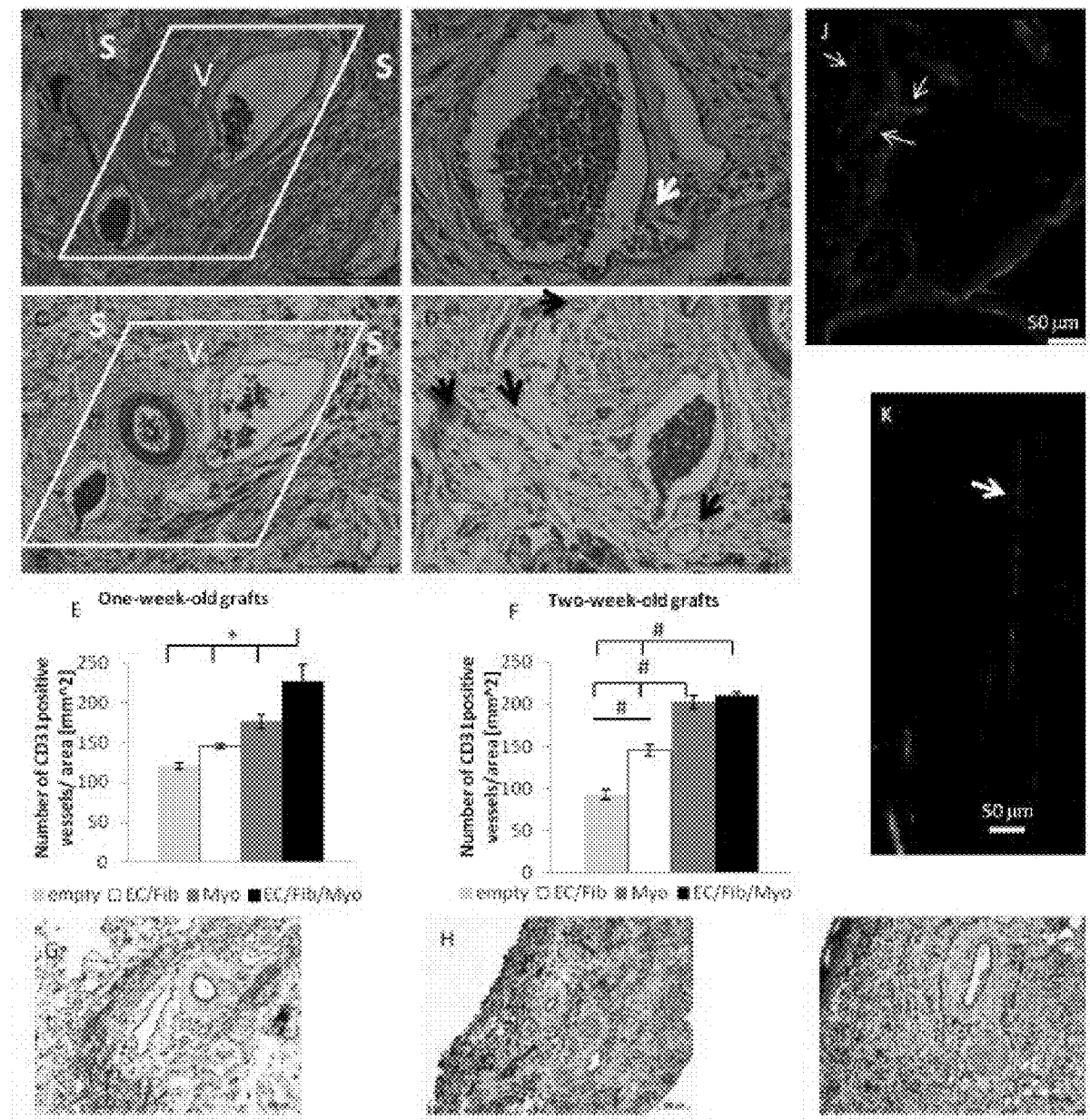
FIG. 2: Sprouting of new functional vessels with red blood cells from the host's femoral artery and vein, toward the engineered tissue graft. (A and B) H&E staining. (C and D) Masson Trichrome representative staining one week postimplantation of the sprouting from the femoral vein towards the engineered tissue. S depicts the scaffold and V depicts the mouse artery and vein. Bar=200 µm. (B) The white arrow points to a host vessel sprouting towards the scaffold. Bar=50 µm. (D) The black arrow points to new capillaries. Bar=100 µm. (E and F) Vascularization quantification of EC/Fib/Myo graft versus EC/Fib, Myo or empty scaffolds. The density of CD31-positive vessels, measured at one (E) and two (F) weeks postimplantation. All values are normalized to the graft's area (mm$^2$). *=p<0.05 according to the results of the post-hoc Student-Newman-Keuls multiple comparisons test; in F, all groups are significantly different from each other (#=p<0.001 according to the results of the post-hoc post hoc Student-Newman-Keuls multiple comparisons test), except for the Myo grafts versus EC/Fib/Myo grafts. For all determinations, the sample size was n>3 and all values are represented as mean±standard error of the mean. (G-I) Representative images of CD31-stained blood vessels in grafts at one-week postimplantation (brown). (G) EC/Fib grafts (H) Myo grafts, and (I) EC/Fib/Myo grafts. The nuclei are stained blue (J-K) Anastomosis between functional human-derived vessels and host (mouse) vessels, identified following a tail-vein-injection of a mixture of rhodamine-conjugated *Ulex europaeus* agglutinin I (UEA-1; red) and fluorescein isothiocyanate-conjugated *Griffonia simplifolia* isolectin B4 (GS-IB4; green). Arrows mark the double staining of UEA-1-stained human and GS-IB4-stained murine blood vessels. Bar=50 µm.

Within one week of implantation, all grafts appeared viable and had already become vascularized (FIG. 1J). New functional blood vessels had sprouted from the AV towards the engineered tissue graft (FIG. 2A-D) and many capillaries were observed in the tissue surrounding the AV, suggesting that the scaffolds had integrated with the host tissue. EC/Fib/Myo grafts were most highly vascularized, as indicated by the mean vasculature density of CD31-positive vessels/mm$^2$ (FIG. 2E), which was significantly higher than that observed in the Myo grafts, the EC/Fib grafts, and empty grafts (FIG. 2G-I). At two weeks post-implantation, both the EC/Fib/Myo and Myo grafts were highly vascularized, with almost the same density of CD31-positive vessels (FIG. 2F), while vascularization of the EC/Fib and empty grafts remained low (FIG. 2F).

An intravenous injection of a mixture of UEA-1 and GS-IB4, was administered in order to determine whether the vascular network of the engineered tissue graft had anastomosed with host vessels and to identify perfused and functional blood vessels[21,22]. Two patterns of double-staining confirmed perfusion within the vessels and included either HUVECs wrapped around host blood vessels, or long human-derived vessels which had anastomosed with host blood vessels (FIG. 2J-K). Most of the blood vessels found in the graft area were mouse-derived vessels.

Example 2

Analysis of Graft Perfusion and Vascularization

Figure 3:
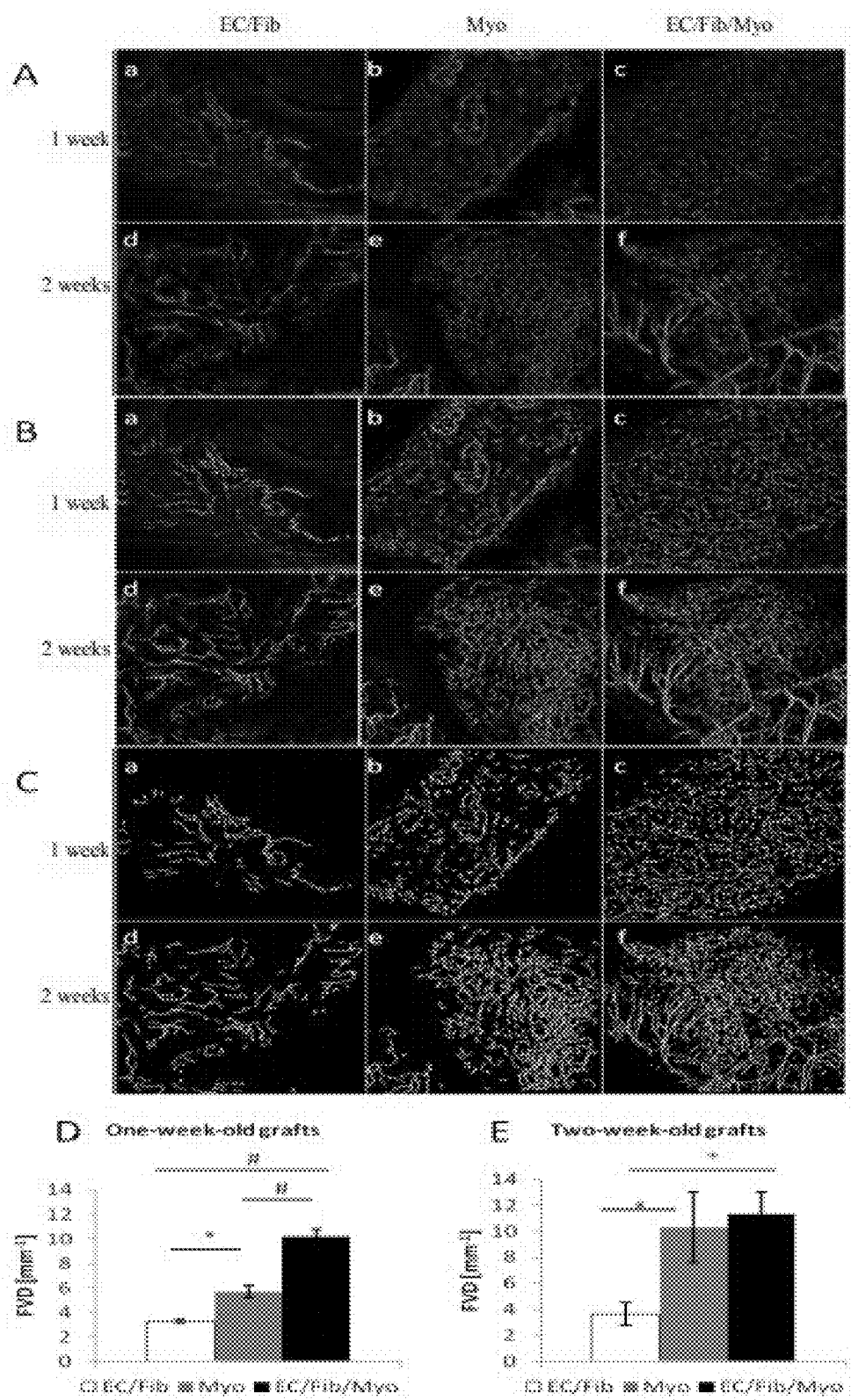
FIG. 3: Representative images of implanted grafts after intravenous injection of fluorescein isothiocyanate-conjugated (FITC)-dextran. (A) Confocal images of EC/Fib, Myo, and EC/Fib/Myo grafts, taken at varying time points after implantation ((a-c) 1 week (d-f) 2 weeks). (B) Image processing by MATLAB: blue lines delineate the region of interest (ROI) in the graft area, red lines delineate the estimated vessel midline, green=FITC-dextran. (C) Binary image after group size filtering. (D and E) Functional vascular density (FVD) of (D) 1-week-old grafts and (E) 2-week-old grafts. *=p<0.05 and #=p<0.01, according to the results of the post-hoc Student-Newman-Keuls multiple comparisons test. For all determinations, the sample size was n≥3 and all values are represented as mean±standard error of the mean.

Vessel patency and the extent of vascularization and of neovasculature within the grafts were assessed by injection of FITC-dextran into the tail vein and analyzing the functional vessel density (FVD) from confocal images of the graft areas (FIG. 3A-C and Supplementary 1 for video of doppler). One week after implantation, the FVD of the EC/Fib/Myo grafts was markedly higher than that of both the Myo grafts and EC/Fib grafts (FIG. 3A-C (a-c) and FIG. 3D). However, two weeks after implantation, the FVD of Myo and EC/Fib/Myo grafts was similar, while the FVD of the EC/Fib grafts remained stable (FIG. 3A-C (d-f) and FIG. 3E).

Figure 4:
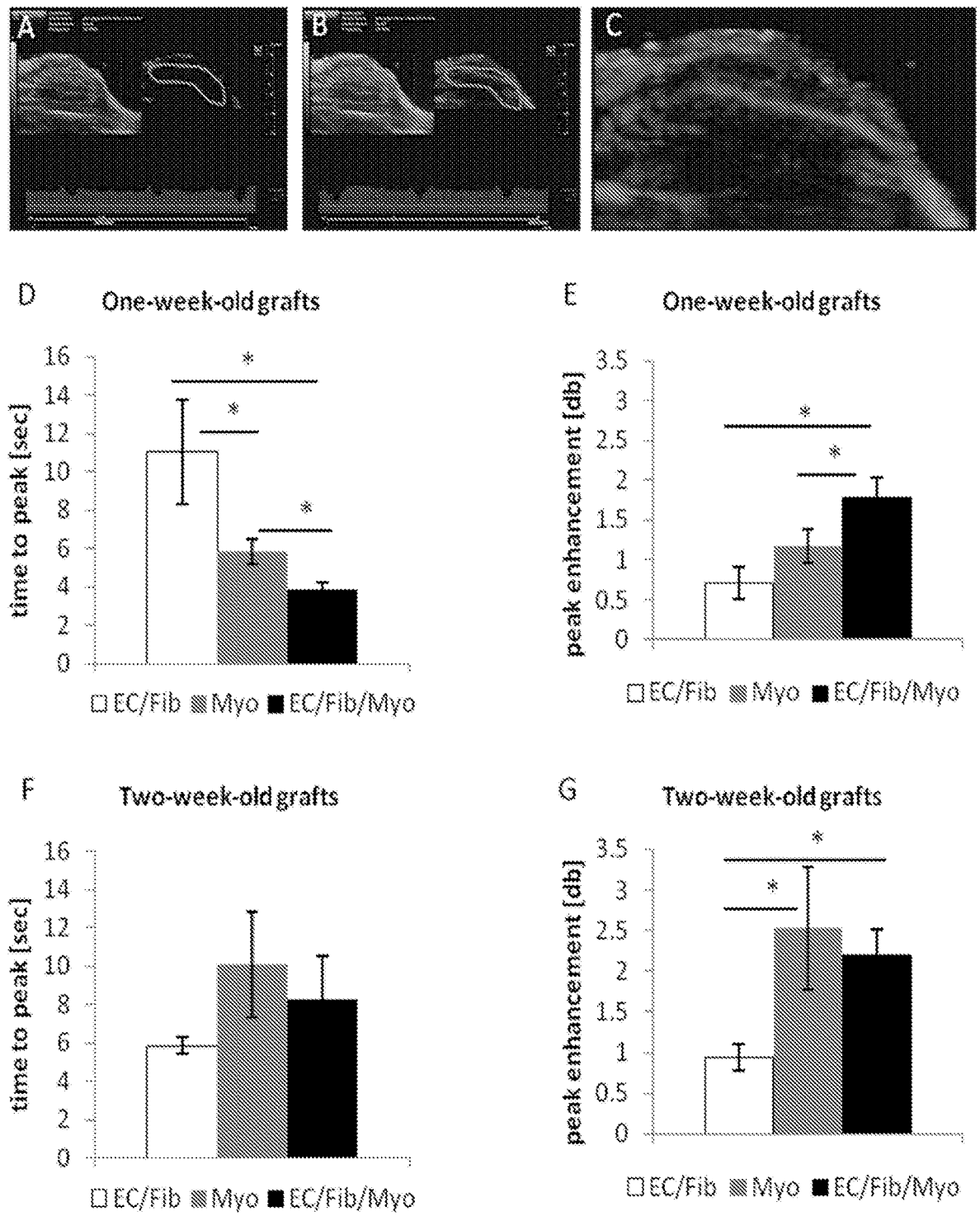
FIG. 4: Ultrasound of EC/Fib, Myo and EC/Fib/Myo grafts following the injection of a contrast agent. (A-C) Representative images of the graft following a tail-vein-injection of microbubble contrast agent. (A) Signal immediately after microbubble destruction, and (B and G) 25 seconds after the injection the contrast agent. C) Magnification of (B). (D and E) 1-week-old grafts. (F and G) 2-week-old grafts. (D and F) Blood flow rate in the grafts. (E and G) Perfusion of the graft. *=p<0.05 according to the results of the post-hoc Student-Newman-Keuls multiple comparisons test. For all determinations, the sample size was n≥3 and all values are represented as mean±standard error of the mean.

Ultrasonigraphic evaluation of graft perfusion rate and the perfused vascular volume demonstrated perfusion within the EC/Fib/Myo grafts at one week and two weeks postimplantation, as expressed by the low number of orange pixels within the graft immediately after the disruption pulse of the micro-bubbles (outlined; FIG. 4A) and a signal increase 25 seconds later (FIG. 4B-C; EC/Fib/Myo grafts and see Supplementary 2 for movie file). At one week postimplantation, both the perfusion rate and the perfused vascular volume within EC/Fib/Myo grafts were higher than those of the Myo and EC/Fib grafts (FIG. 4D-E). At two weeks after implantation, the perfused vascular volume in the EC/Fib/Myo and Myo was higher as compared to immediately after the disruption pulse, and was significantly higher than in EC/Fib grafts, suggesting that the presence of myoblasts promotes graft vasculogenesis. Despite this improved perfused vascular volume, the perfusion rate in the three types of grafts did not significantly differ from one another at this time point (FIG. 4F-G).

Example 3

Flap Transfer and Macroscopic Analysis of the Transferred Flap

The viability of the flaps following their transfer to a full-thickness defect in the abdomen was assessed (FIG. 1J-K). One week after their transfer, flaps derived from cell-populated scaffolds were viable, as evidenced by their red color (FIG. 1L). In contrast, empty scaffolds became necrotic (FIG. 1M-N) and in some instances, led to animal death due to herniation of the abdominal organs.

Figure 5A:
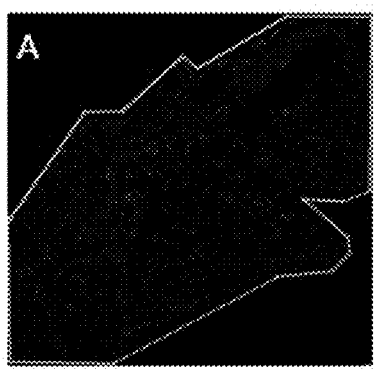
FIG. 5: The extent of vascularization of EC/Fib, Myo, and EC/Fib/Myo flaps as measured by murine CD31-positive staining. (A-C) Image processing of the mCD31-positive vessels by MATLAB: (A) white lines delineate the ROI in the flap. (B) Final image after processing. (C) Zoom-in on the selected area in B; different colors represent the different circumferences of the blood vessels. (D-E) Flaps derived from 1-week-old engineered tissue grafts. (F-G) Flaps derived from 2-week-old engineered tissue grafts. (D and F) mCD31-positive vessels; all values were normalized to the scanned area of the flap in mm$^2$. (E and G) Histograms of the circumference of the vessels in the flaps (x-axis), expressed as a percentage of the total number of vessels in the graft (y-axis). *=p<0.05 and #=p<0.01 according to the results of the post-hoc Student-Newman-Keuls multiple comparisons test. For all determinations, the sample size was ≥3 and all values are represented as mean±standard error of the mean.
Figure 5B:
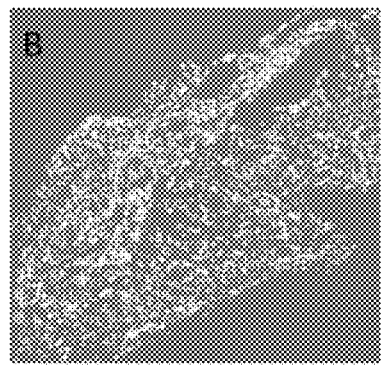
Figure 5C:
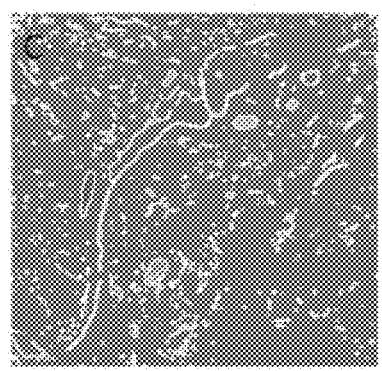
Figure 5D:
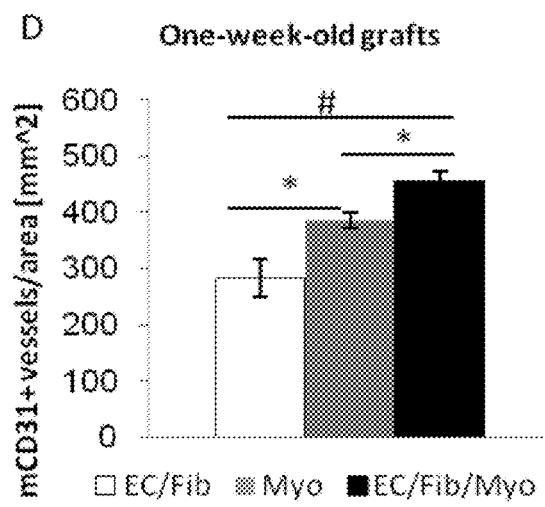
Figure 5E:
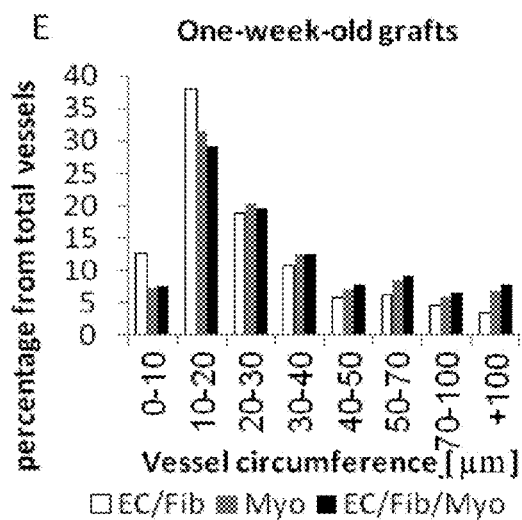
Figure 5F:
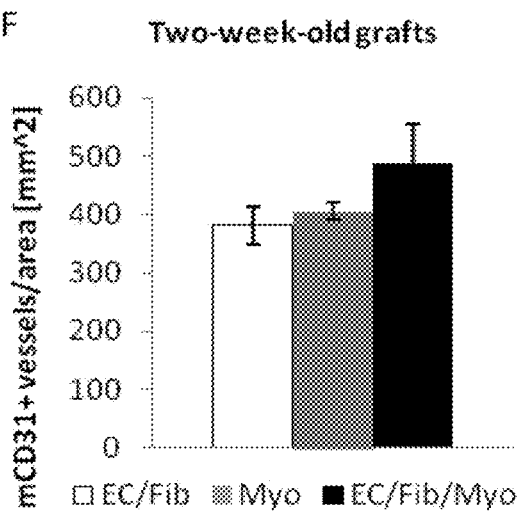
Figure 5G:
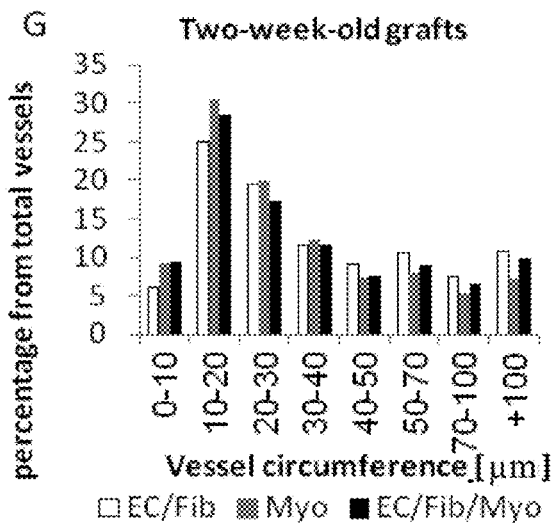

Since most of the functional blood vessels in the transferred flap were of mouse origin, next it was determined the extent of flap vascularization by means of mCD31 staining. mCD31-stained and H&E-stained flap sections revealed the presence of many capillaries within the flaps (FIG. 5A-C and Supplementary 3d-f). Erythrocytes were seen in the main artery and in smaller vessels that supplied the flaps, indicating that the flap vessels remained intact during transfer. When transferred one week after implantation, the extent of vascularization in the EC/Fib/Myo flaps was greater than that of the Myo and EC/Fib flaps (FIG. 5D). Moreover, the circumference of vessels in the EC/Fib/Myo flaps was larger than those within EC/Fib flaps (FIG. 5E). In contrast, when transferred two weeks after implantation, the extent of flap vascularization did not significantly differ between the flaps (FIG. 5F-G). The extent of vascularization within empty scaffolds was not determined because they had either necrosed or the mice had died within 2-5 days.

Examination of desmin- and Masson's trichrome (MT)-stained sections revealed that there were 25.2±10.4 and 4.62±3.26 more desmin positive staining in the Myo and EC/Fib/Myo flaps than in the EC/Fib flaps, one and two weeks postimplantation, respectively (Supplementary 3 a-c and g-i). In the EC/Fib flaps, desmin-stained fibroblasts which had differentiated into smooth muscle cells, were located around CD31-positive vessels (Supplementary 3 g). MT-stained sections of all flaps transferred one week after graft implantation, included myogenic cells at the flap edges proximal to the host tissue (Supplementary 3A(a-c)). Examination of the desmin-stained Myo and EC/Fib/Myo flaps transferred at one-week postimplantation, revealed the presence of myogenic cells also in the center of the flap, next to its vasculature (Supplementary 3A(g-i)). Although most of these myogenic cells were young myoblasts, originating from either seeded myoblasts or invading host cells, elongated and aligned myocytes were also observed (Supplementary 3h and i). Moreover, most of the myogenic cells in the EC/Fib/Myo flaps were aligned and elongated (Supplementary 3A(i)). Examination of the MT- and desmin-stained sections of Myo flaps transferred two weeks after graft implantation, revealed the presence of aligned and elongated myoblasts (Supplementary 3B(h)). In the EC/Fib/Myo flaps, mature myocytes, were observed (Supplementary 3B(i)), suggesting more efficient integration of EC/Fib/Myo flaps with the host tissue than i n other flap types.

Mechanical Flap Properties

During flap extraction attempts one-week post transfer, EC/Fib/Myo flaps demonstrated firm attachment to the surrounding tissue when compared to the control groups. Moreover, wound dehiscence and herniation occurred less frequently in EC/Fib/Myo flaps as compared to the control groups. Evaluation of the tensile strength of the flaps (FIG. 6A-B) demonstrated that flaps derived from EC/Fib/Myo scaffolds bore the highest tensile strength (FIG. 6C). Myo flap stiffness was greater than that of flaps derived from the empty scaffolds, but was less than that of EC/Fib flaps (FIG. 6C). Similarly, the highest UTS was measured for EC/Fib/Myo flaps, while flaps derived from empty scaffolds, yielded the lowest UTS (FIG. 6D). Myo flaps featured a higher UTS than EC/Fib flaps. Overall, these results suggest that the presence of endothelial cells and myoblasts in the flaps is critical for the final strength and the stiffness of the fabricated tissue.

Reconstruction of complex wall defects caused by either trauma or following tumor ablation, present major challenges. Although a wide variety of biological[10-12] and synthetic matrices[1,8,9] have been investigated for hernia repair, their use is limited when skin coverage is inadequate, as in case of full-thickness defects. In parallel, contemporary surgical techniques exploiting local, regional or free flaps, present drawbacks, such as donor-site morbidity, procedure duration and the often scant availability of tissues in the area of the defects. Thus, while use of free flaps can address the requirements of full-thickness defects, it requires longer surgery and higher surgical skill.

In the present study, a novel method for repair of a large soft tissue defect, using an engineered tissue-based flap was designed and investigated. The prefabricated graft was implanted around the AV and isolated from its suroundings. The graft proved viable, vascularized, and perfused, and contained blood vessels which anastomosed with host blood vessels. Following transfer of the flap to the full-thickness defect, the sample remained viable, vascularized, and became well integrated within the surrounding tissue. EC/Fib/Myo scaffold-derived flaps outperformed all other flap types in their degree of vascularization, perfusion, mechanical properties, and tissue integration within the host. Thus, usage of an engineered tissue with a functional host blood vessel network can circumvent the need for transfer of massive tissue volumes from another site, and avoid postoperative scarification of the donor site.

Proper flap vascularization is essential for its successful integration within the host. Various approaches have been used to create vascularized engineered tissue in order to improve oxygen supply and diffusion in thick tissues. Dvir et al. constructed a vascularized cardiac patch, using both survival and angiogenic factors, by first implanting the patch on the omentum. Controlled delivery of proangiogenic factors from growth factor-eluting scaffolds has been shown to induce host vessels ingrowth into the implant, while EC seeding has been attempted to promote further vascularization upon implantation. EC-embedded scaffolds underwent improved integration within the host tissues after implantation. Higher amount of tissue or even a whole organ can be implanted, when fabricating a tissue with blood vessels' net which then can be connected to the main trunk, by connecting the blood vessel of the engineered tissue to host vessels.

Figure 7:
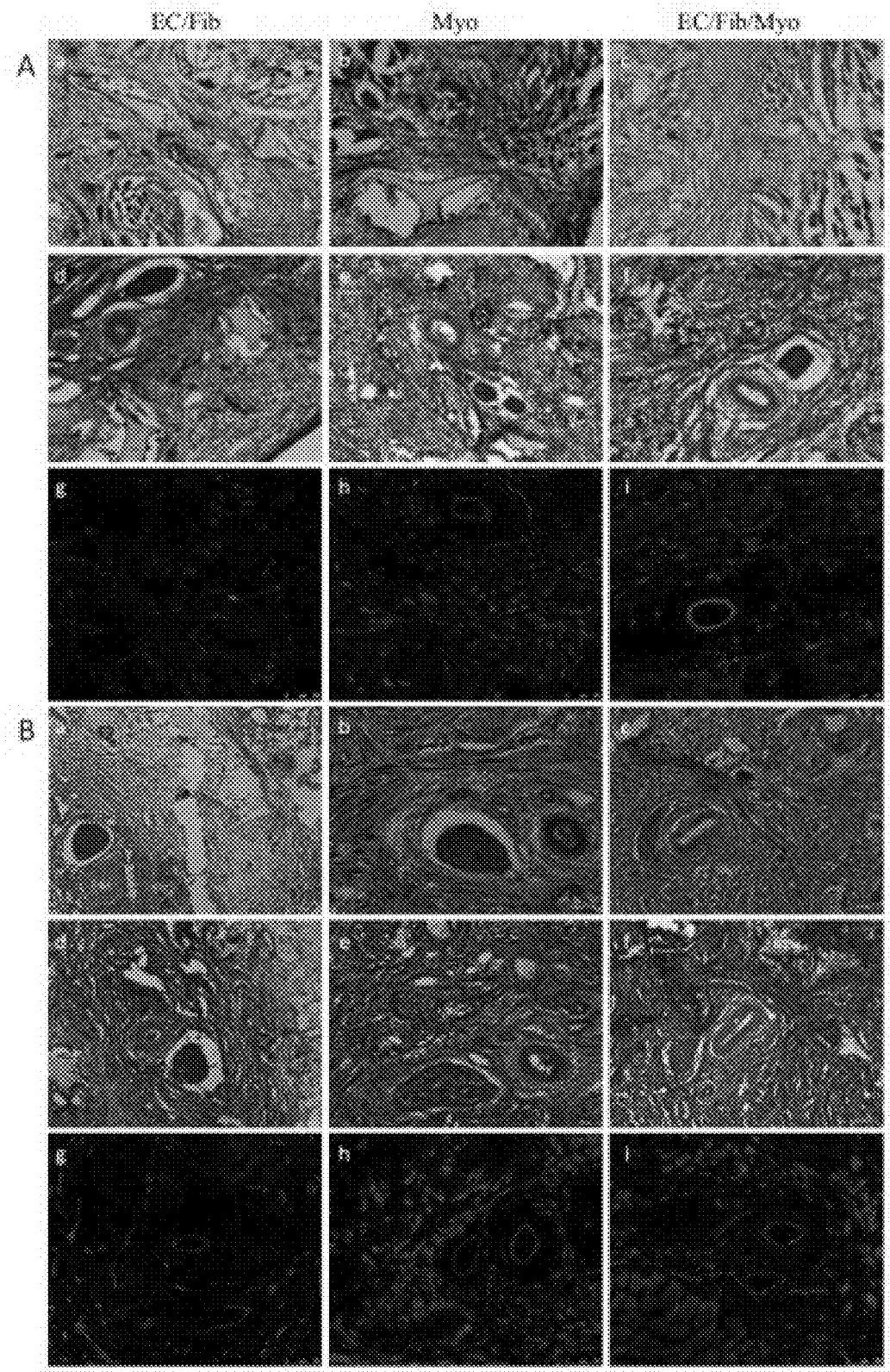
FIG. 7: Representative images of histological stainings of transferred flaps. Flaps transferred (A) one-week or (B) two-weeks postimplantation. (a-c) Masson's trichrome (MT) staining, X10, scale bar=100 µm. (d-f) Hematoxylin and eosin (H&E) staining, X10, scale bar=100 µm. (g-i) Immunofluorescent staining: murine CD31-positive staining (green), desmin-positive staining (red). The nuclei are stained blue, scale bar=100 µm.

The extensive vascularization and perfusion in Myo grafts stand in line with previous reports of C2C12 cells which can secrete angiogenic factors (including VEGF), and stimulate vascularization of the surrounding tissue. The FVD of Myo grafts which was higher than that of EC/Fib grafts, seemingly due to the large number of small and immature blood vessels which may be contributed by C2C12 angiogenic factors secretion. In parallel, ECs and fibroblasts have also been reported to secrete VEGF. In line with these works, the addition of ECs significantly promoted flap vascularization and viability following transfer. It was shown that the EC-driven blood network, generated in vitro, became functional and integrated with the host vessels upon implantation. EC/Fib/Myo flap underwent the most effective integration and induced the most advanced regeneration of host tissue (FIG. 7), when compared to the other tested flaps. Further investigation will be necessary to uncover the main role of ECs in the engineered tissue, particularly, to determine to what extent the ECs physically participate in the blood vessel network formation in vivo or if their impact is mainly via secretion of VEGF and other growth factors following graft transfer.

The presented work demonstrated that the cell types integrated in the engineered flaps dictate its mechanical strength. Specifically, EC/Fib/Myo flaps were stiffer and stronger than EC/Fib, Myo, and empty flaps. It was observed that wound dehiscence and herniation occurred less frequently in mice treated with the EC/Fib/Myo flaps, when compared to animals treated with other flaps, which was attributed to the increased mechanical strength of the transplanted tissue.

When myotubes are formed, the myocytes become vascularized, innervated, and finally mature as myofibers, which are then packed together by connective tissue in order to provide mechanical strength to the muscle. Muscle cell alignment and elongation are crucial steps in muscle regeneration. The final strength of muscle tissue is derived from the parallel organization of the myotubes within the muscle tissue. It has also been shown that vascularization of skeletal muscle is essential for muscle regeneration. Indeed, it was observed mature and aligned myoblasts in the EC/Fib/Myo flaps, suggesting the mechanism which supports more rapid muscle regeneration.

It is worth mentioning that the host's peripheral vessels, and not the femoral artery and vein, as used in this investigation, can be exploited to fabricate the described flap for repair of large tissue defects in large animals. The results of this study provide experimental evidence for the requirement of tissue-specific cells (i.e., myoblasts), as well as ECs and fibroblasts, in successful engineering muscle flap. Furthermore, these results emphasize the need for functional vessels in flaps applied to full thickness defects. Specifically, it was shown that EC/Fib/Myo flaps became more vascularized by host blood vessels and were more rapidly and more effectively integrated within the host tissue than EC/Fib or Myo flaps.

Example 4

Connective Tissue Flap Endothelial and Mesenchymal Cells

Human Adipose Microvascular Endothelial Cells (HAMEC) and Mesenchymal Stem Cell (MSC) were co-cultured on a PLLA/PLGA scaffold. HAMEC and MSC were cultured in a ratio of 5:1, respectively, on 2 cm×1 cm scaffold for 7 days in vitro. Controls groups included only HAMEC and only MSC using the same concentration of each cell type upon the scaffold.

Figure 8:
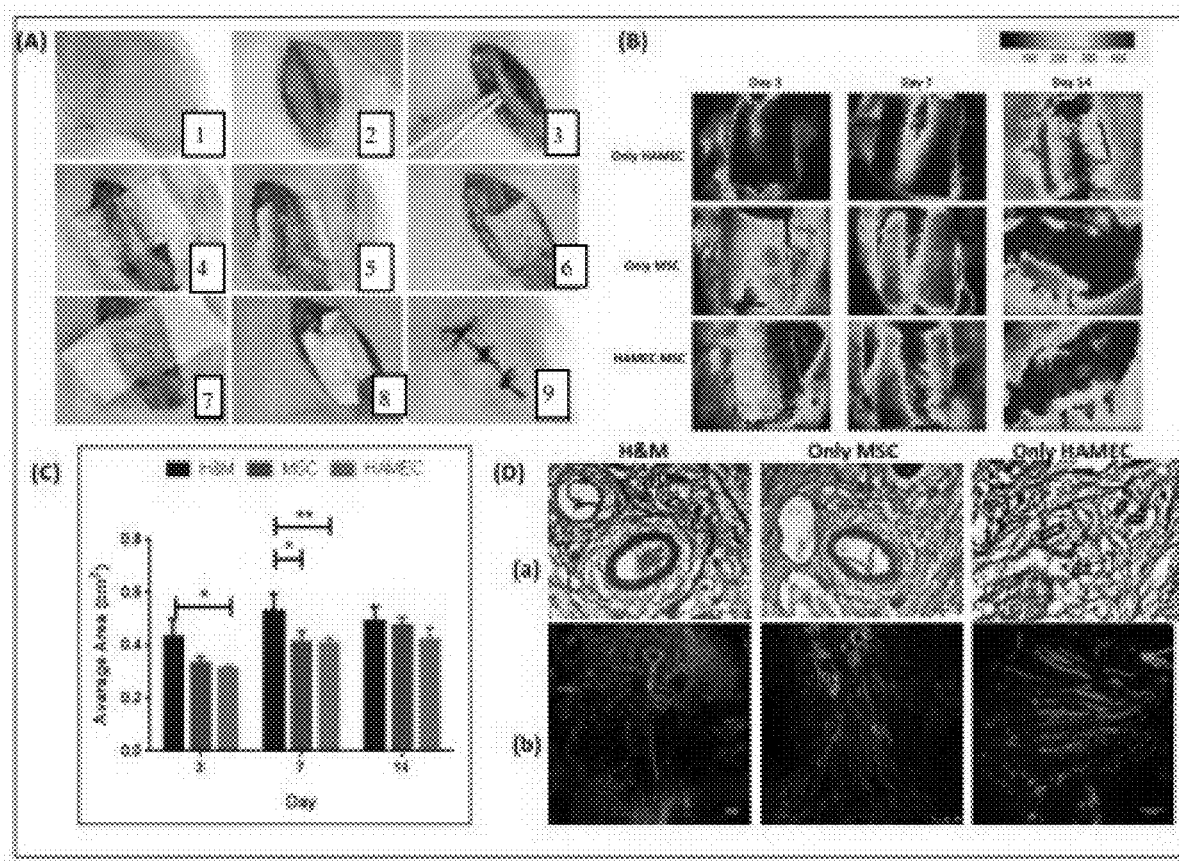
FIG. 8: Engineered Vascularized Graft In Vivo (see also example 4). (A) is a micrograph showing surgical procedure of vascularized scaffold implantation in femoral AV of a rat: (1-3) Isolation of the femoral AV from the surrounding tissue. (4-6).The fabricated tissue graft was folded around the blood vessels and sutured. (7-8). The fabricated graft was separated from the surrounding tissue and wrapped by a sterile latex which was then sutured. (9) Suturing the overlying skin. (B) is a micrograph showing flux images taken via Laser Speckle of implanted grafts in different time points (3, 7, 14) for the 3 observed groups. The color scale indicates the intensity of the flux in the formed vessels. (C) is a graph showing statistical analysis of flux results shown in (B) represent the Average Area of the total flux depicted in the flux images. Results are reported as Mean±SEM. (D) is a micrograph showing: (a) H&E staining shows formation of arteries pointed by white arrows and bigger veins; (b) Immuno-fluorescent staining using anti-rat Lectin (Green) and DAPI.

On day seven, scaffolds were implanted around the femoral artery and vain (AV) in rats. In order to make sure that anastomosis were induced only by the AV, the implanted scaffold was wrapped with sterile latex. Vessel formation has been monitored by measuring blood flux via Laser Speckle instrument in different time points (3, 7 and 14 days, see FIG. 8). Following that, animals were sacrificed in order to continue vascularization analyses in the graft.

Likewise, the same procedure was performed in order to use the vascularized graft for transferring it as a flap (implant) to a full defect made in the leg. The viability of the transferred graft has been monitored also by Laser Speckle instrument (see FIG. 8).

Figure 9:
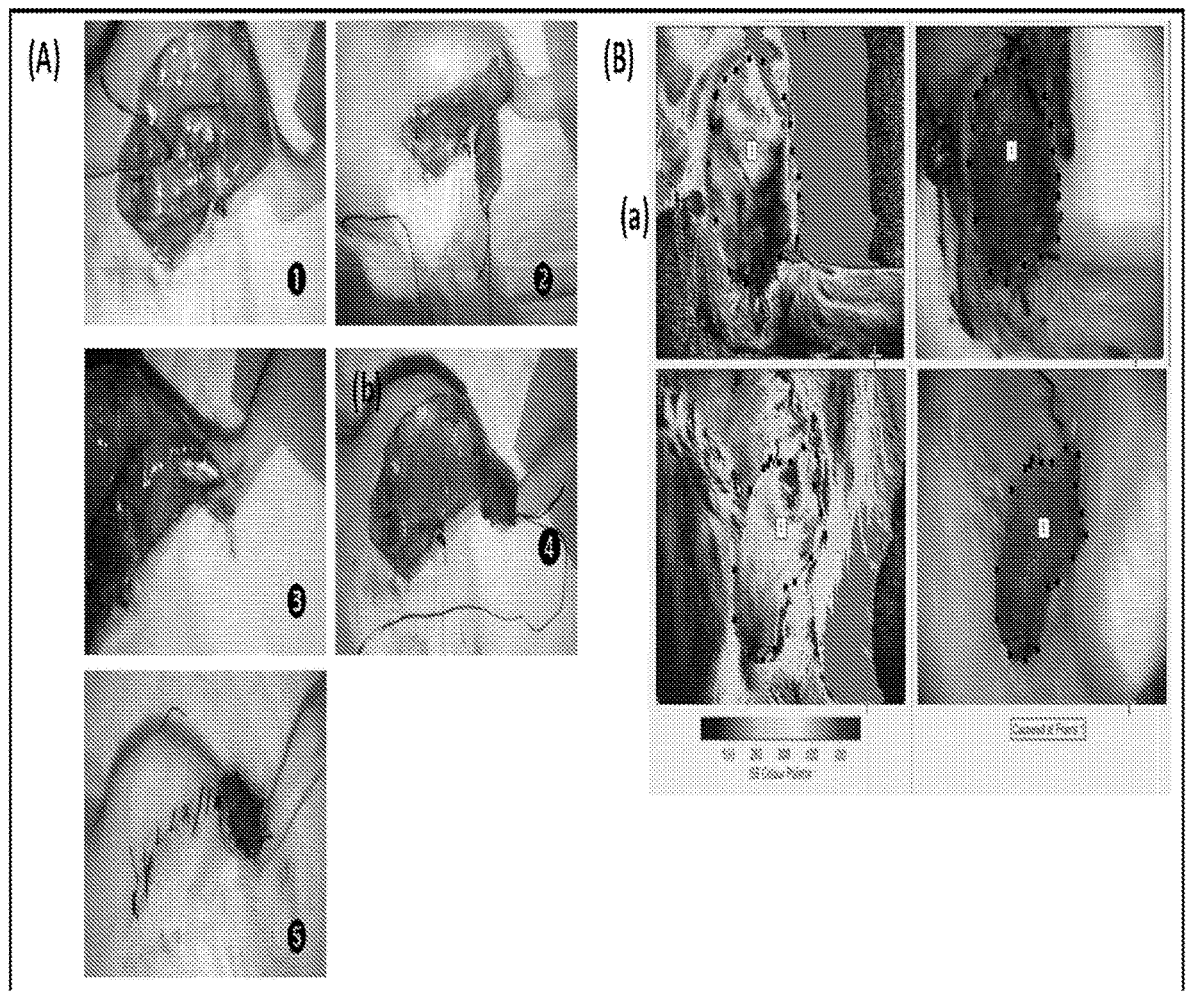
FIG. 9: In Vivo Axial Flap (see also example 4) (A) is a micrograph showing surgical procedure of axial flap towards exposed bone defect in the leg of a rat. (1) Representative image of a fabricated tissue graft 5 weeks post implantation. (2) Isolation of the graft from the surrounding tissue (3) Making a full defect by exposing the bone (4) Transfer of the graft as axial flap towards the exposed bone. (5) Suturing the skin and exposing the flap to the air. (B) is a micrograph showing flux and images: (a) one day post flap transfer (b) six days post flap transfer; the engineered graft remains viable and vascularized.

Axial Flap procedure involved a transfer of the graft towards exposed bone in the leg (see FIG. 9). The procedure induced blood flow thus nurturing the graft which in turn allowed the exposed bone to be protected and fed by the vascularized flap. In this experiment the flap remained exposed to air in order to mimic a scenario of massive skin loss in humans.

What is claimed is:

1. An implant comprising: (a) an engineered tissue; and (b) a sterile latex wrapping around said engineered tissue; and (c) vasculature comprising a vein and an artery, wherein said engineered tissue comprises a wrappable inorganic porous scaffold embedded with a myoblast, a mesenchymal stem cell and an endothelial cell, or an endothelial cell, a myoblast and a fibroblast wherein said porous scaffold is wrapped around said vasculature, said vasculature feeds said cells and said engineered tissue comprises a blood vessel with an inner circumference of between 40-100 micrometers (μm).

2. The implant of claim 1, wherein said porous scaffold comprises poly-l-lactic acid (PLLA) and polylactic-co-glycolic-acid (PLGA).

3. The implant of claim 1, wherein said implant's volume is between 8 and 100 cm$^3$.

4. The implant of claim 1, wherein said porous scaffold comprises pores having a diameter of 150 to 800 μm.

5. The implant of claim 1, wherein said porous scaffold comprises at least 85% porosity.

6. The implant of claim 1, wherein said porous scaffold comprises fibrin, fibronectin, thrombin, or any combination thereof.

7. The implant of claim 1, wherein said engineered tissue comprises a myoblast, an endothelial cell, and a fibroblast; and comprises a blood vessel with an inner circumference of between 70-100 μm.

8. The implant of claim 1, wherein said porous scaffold is a sponge.

9. The implant of claim 1, wherein said porous scaffold is a sheet wrapped around said vasculature.

10. The implant of claim 1, wherein said engineered tissue comprises endothelial cells, fibroblasts and myoblasts.

11. The implant of claim 10, wherein said engineered tissue comprises a greater number of endothelial cells than myoblasts and a greater number of myoblasts than fibroblasts.

12. The implant of claim 10, wherein said implant is characterized by an ultimate tensile strength of at least 50 kilopascals (kPa).

13. The implant of claim 1, wherein said engineered tissue comprises endothelial cells, myoblast and mesenchymal stem cells (MSCs).

14. The implant of claim 13, wherein there said engineered tissue comprises a greater number of endothelial cells than MSCs.

* * * * *